US012672757B2

(12) United States Patent
    Hane

(10) Patent No.: US 12,672,757 B2
(45) Date of Patent: Jul. 7, 2026

(54) ENDOSCOPE SYSTEM, LUMEN STRUCTURE CALCULATION SYSTEM, AND METHOD FOR CREATING LUMEN STRUCTURE INFORMATION

(71) Applicant: OLYMPUS MEDICAL SYSTEMS CORP., Tokyo (JP)

(72) Inventor: Jun Hane, Tokyo (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 260 days.

(21) Appl. No.: 18/384,975

(22) Filed: Oct. 30, 2023

(65) Prior Publication Data

US 2024/0057847 A1     Feb. 22, 2024

Related U.S. Application Data

(63) Continuation of application No. PCT/JP2021/017141, filed on Apr. 30, 2021.

(51) Int. Cl.
    *A61B 1/00*          (2006.01)
    *G06T 7/60*          (2017.01)
            (Continued)

(52) U.S. Cl.
    CPC .......... *A61B 1/000094* (2022.02); *G06T 7/60* (2013.01); *G06T 7/73* (2017.01);
            (Continued)

(58) Field of Classification Search
    None
    See application file for complete search history.

(56) References Cited

U.S. PATENT DOCUMENTS 6,063,023 A      5/2000  Sakiyama et al.
2009/0220133 A1  9/2009  Sawa et al.
            (Continued)

FOREIGN PATENT DOCUMENTS

JP      H10248806 A      9/1998
JP      2008048906 A     3/2008
            (Continued)

OTHER PUBLICATIONS

Japanese Office Action dated Nov. 26, 2024 received in 2023-516988.

(Continued)

*Primary Examiner* — Edward Martello
(74) *Attorney, Agent, or Firm* — Scully, Scott, Murphy & Presser, P.C.

(57)          ABSTRACT

An endoscope system includes an insertion section, an imager, and a control device including a processor that processes a signal from the imager. The insertion section is inserted into a lumen as an object. The imager is monocular and is provided in the insertion section to capture an image of the object. The processor acquires actual size determination information for determining an actual size of at least a portion of the lumen. The processor calculates a three-dimensional structure of the lumen based on the captured image. The processor also calculates three-dimensional structure size information for determining an actual size of at least a portion of the three-dimensional structure by calibrating the three-dimensional structure of the lumen based on the actual size determination information. The processor also outputs specific portion size information representing an actual size of a specific portion of the three-dimensional structure, based on the three-dimensional structure size information.

24 Claims, 21 Drawing Sheets

(51) Int. Cl.

| | | |
|---|---|---|
| *G06T 7/73* | (2017.01) | |
| *G06T 7/90* | (2017.01) | |
| *G06T 17/00* | (2006.01) | |

(52) U.S. Cl.

CPC ................ *G06T 7/90* (2017.01); *G06T 17/00* (2013.01); *G06T 2207/10068* (2013.01); *G06T 2210/41* (2013.01)

(56) References Cited

U.S. PATENT DOCUMENTS

| | | |
|---|---|---|
| 2010/0034443 A1 | 2/2010 | Inoue |
| 2016/0287141 A1 | 10/2016 | Sidlesky |
| 2018/0214006 A1 | 8/2018 | Akimoto et al. |
| 2018/0342074 A1 | 11/2018 | Sakamoto |
| 2020/0060528 A1 | 2/2020 | Akimoto |

| | | | |
|---|---|---|---|
| 2020/0279373 A1* | 9/2020 | Hussain | ................. G16H 50/70 |
| 2020/0281454 A1 | 9/2020 | Refai et al. | |
| 2024/0013389 A1* | 1/2024 | Usuda | ................... G06T 7/0012 |

FOREIGN PATENT DOCUMENTS

| | | | |
|---|---|---|---|
| JP | 2017508529 | A | 3/2017 |
| JP | 2018197674 | A | 12/2018 |
| JP | 6478136 | B1 | 3/2019 |
| WO | 2008136098 | A1 | 11/2008 |
| WO | 2017057330 | A1 | 4/2017 |
| WO | 2018230098 | A1 | 12/2018 |

OTHER PUBLICATIONS

International Search Report dated Jul. 13, 2021 issued in PCT/JP2021/017141.

* cited by examiner

FIG.4

ENDOSCOPE SYSTEM, LUMEN STRUCTURE CALCULATION SYSTEM, AND METHOD FOR CREATING LUMEN STRUCTURE INFORMATION

CROSS REFERENCE TO RELATED APPLICATIONS

This application is a continuation of International Patent Application No. PCT/JP2021/017141, having an international filing date of Apr. 30, 2021, which designated the United States, the entirety of which is incorporated herein by reference.

BACKGROUND OF THE INVENTION

The size of a lesion, such as a polyp, a cancer, or the like, has been used for determination as to whether or not to perform treatments or for determination of the treatment method. Therefore, it is desirable to determine the size of the lesion detected during an examination in which an endoscope is inserted into the body of a subject. Japanese Unexamined Patent Application Publication No. H10-248806 discloses a measurement endoscope device that performs measurement by image processing using endoscope images obtained by a pair of objective lenses.

SUMMARY OF THE INVENTION

In accordance with one of some aspect, there is provided an endoscope system comprising:

an insertion section configured to be inserted into a lumen as an object;

a monocular imager provided in the insertion section and configured to capture an image of the object; and a control device including a processor that processes a signal from the imager, wherein the processor is configured to:

acquire actual size determination information for determining an actual size of at least a portion of the lumen;

calculate a three-dimensional structure of the lumen based on the captured image;

calculate three-dimensional structure size information for determining an actual size of at least a portion of the three-dimensional structure by calibrating the three-dimensional structure of the lumen based on the actual size determination information; and output specific portion size information representing an actual size of a specific portion of the three-dimensional structure, based on the three-dimensional structure size information.

In accordance with one of some aspect, there is provided a lumen structure calculation system comprising a processor including hardware, wherein the processor acquires a captured image of an object acquired by a monocular imager provided in an insertion section, which is inserted into a lumen as the object, and actual size determination information, which is information for determining an actual size of at least a portion of the lumen, calculates a three-dimensional structure of the lumen based on the captured image, calculates three-dimensional structure size information for determining an actual size of at least a portion of the three-dimensional structure by calibrating the three-dimensional structure of the lumen based on the actual size determination information, and outputs specific portion size information representing an actual size of a specific portion of the three-dimensional structure, based on the three-dimensional structure size information.

In accordance with one of some aspect, there is provided a method for creating lumen structure information comprising:

acquiring a captured image of an object acquired by a monocular imager provided in an insertion section, which is inserted into a lumen as the object;

acquiring actual size determination information, which is information for determining an actual size of at least a portion of the lumen;

calculating a three-dimensional structure of the lumen based on the captured image;

calculating three-dimensional structure size information for determining an actual size of at least a portion of the three-dimensional structure by calibrating the three-dimensional structure of the lumen based on the actual size determination information; and outputting specific portion size information representing an actual size of a specific portion of the three-dimensional structure, based on the three-dimensional structure size information.

BRIEF DESCRIPTION OF THE DRAWINGS

FIG. 4 is a block diagram explaining another configuration example of an endoscope system.

DETAILED DESCRIPTION

Figure 1:
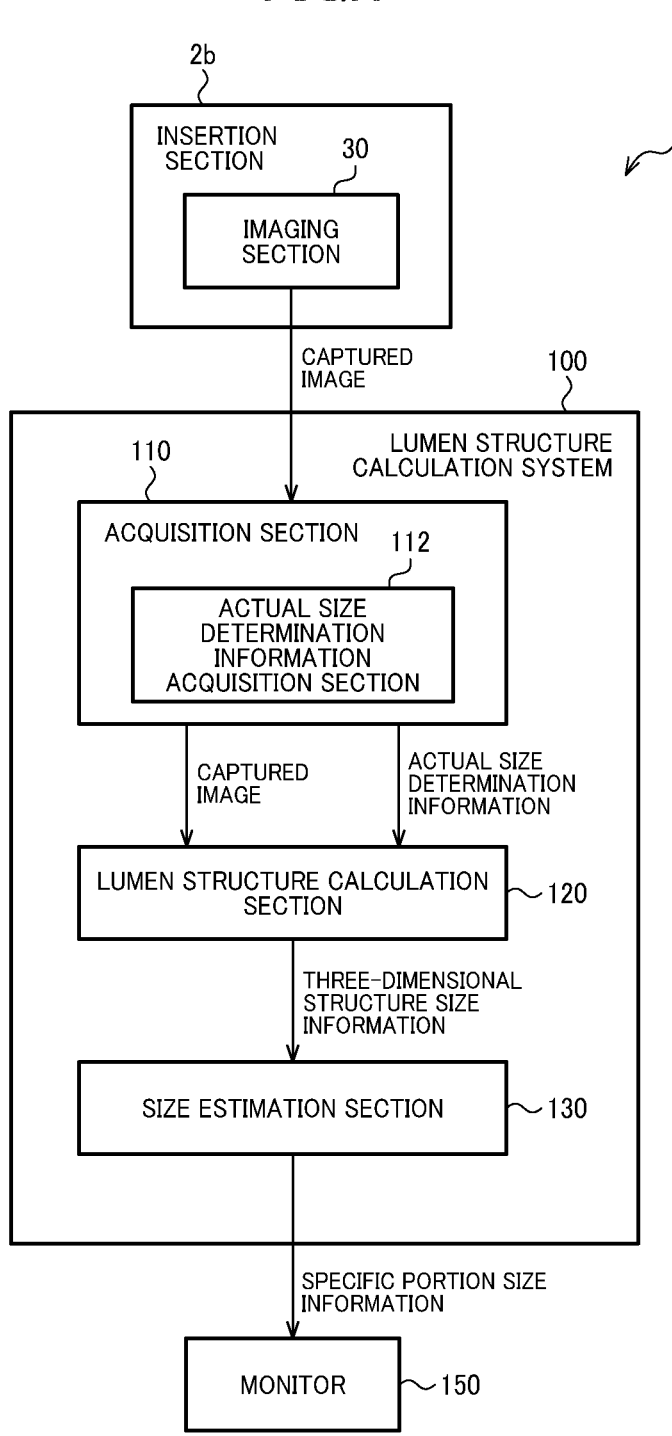
FIG. 1 is a block diagram explaining a configuration example of an endoscope system.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

The present embodiment is described below. Note that the present embodiment described below as an exemplary embodiment does not in any way limit the scope of the content defined by the claims laid out herein. Note also that all of the structures described in the present embodiment should not necessarily be taken as essential structural components of the present disclosure.

An endoscope system 1 of the present embodiment is described below with reference to FIGS. 1, 2, and 3. FIG. 1 is a block diagram explaining a configuration example of the endoscope system 1 of the present embodiment. The endoscope system 1 includes an insertion section 2b and a lumen structure calculation system 100. The insertion section 2b includes an imaging section 30. The lumen structure calculation system 100 includes an acquisition section 110, a lumen structure calculation section 120, and a size estimation section 130. The acquisition section 110 includes an actual size determination information acquisition section 112. That is, the endoscope system 1 of the present embodiment includes the insertion section 2b, the imaging section 30, the acquisition section 110, the lumen structure calculation section 120, and the size estimation section 130. The structure of the endoscope system 1 is not limited to the structure shown in FIG. 1, and can be modified in various ways including adding other components. The details of the variation will be described later.

Figure 2:
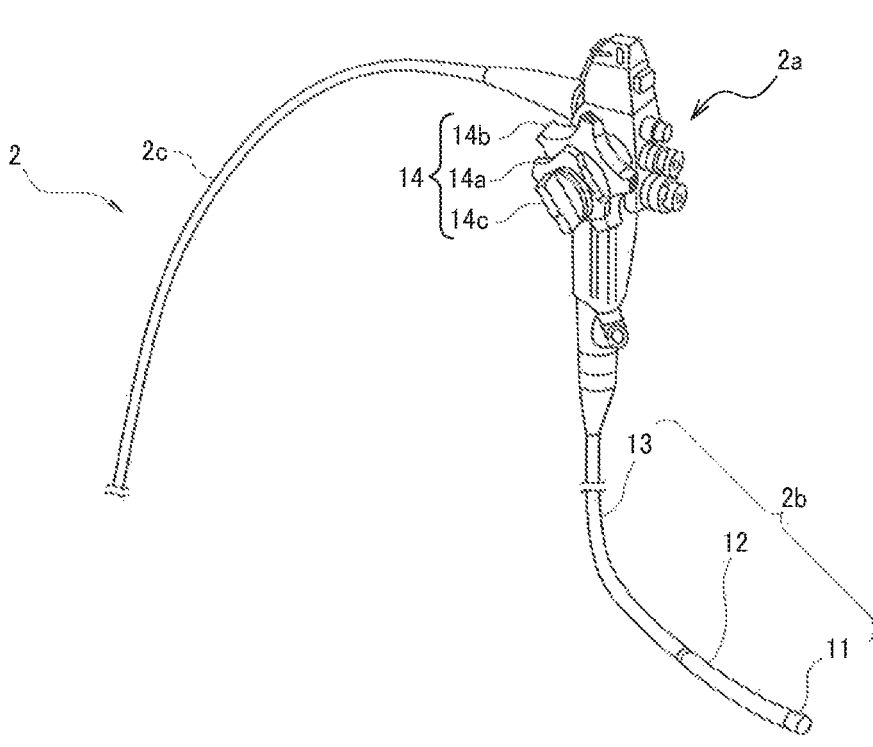
FIG. 2 is a perspective view explaining an example of endoscope.

FIG. 2 is a perspective view explaining an example of an endoscope 2 of the present embodiment. The endoscope 2 has an operation section 2a, a flexible insertion section 2b, a universal cable 2c including such as signal lines. The endoscope 2 is a tubular insertion device with the tubular insertion section 2b to be inserted into a lumen. A connector is provided at the distal end of the universal cable 2c, and the endoscope 2 is detachably connected to a light source device 4 and the like, which is described later with reference to FIG. 6, by the connector. Further, although not shown in the figure, a light guide is inserted inside the universal cable 2c, and the endoscope 2 emits illumination light, which is emitted from the light source device, from the distal end of the insertion section 2b through the light guide. Although the following explanation will describe an example in which the surgeon inserts the endoscope 2 into the large intestine of the patient Pa, the location where the endoscope 2 is inserted is not limited to the large intestine. Further, the surgeon is, for example, a doctor, and the doctor is, for example, an endoscopist.

As shown in FIG. 2, the insertion section 2b has, from the distal end to the base end of the insertion section 2b, a distal end section 11, a curving section 12 that is curvable, and a flexible tube section 13. The insertion section 2b is inserted into the lumen of the patient Pa, who is an object of image capturing. The base end section of the distal end section 11 is connected to the distal end of the curving section 12, and the base end section of the curving section 12 is connected to the distal end of the flexible tube section 13. The distal end section 11 of the insertion section 2b is the distal end section of the endoscope 2, which is a hard rigid distal end.

The curving section 12 is made curvable in a desired direction according to the operation with respect to a curving operation member 14 provided in the operation section 2a. The curving operation member 14 includes, for example, a left/right curving operation knob 14a and an up/down curving operation knob 14b. When the curving section 12 is curved and the position and the direction of the distal end section 11 are changed to capture an observation portion inside the subject within a field of view, the illumination light is emitted to the observation portion. The curving section 12 has a plurality of curving pieces that are coupled along the longitudinal axis direction of the insertion section 2b. Therefore, the surgeon can observe the inside of the large intestine of the patient Pa by curving the curving section 12 in various directions while pushing the insertion section 2b into the lumen of the large intestine or the like or pulling it out of the lumen.

The left/right curving operation knob 14a and the up/down curving operation knob 14b cause an operation wire inserted inside the insertion section 2b to pull and relax in order to curve the curving section 12. The curving operation member 14 further has a fixing knob 14c to fix the curved position of the curving section 12. The operation section 2a is also provided with various operation buttons such as a release button, an air/water supply button, and the like, in addition to the curving operation member 14.

The flexible tube section 13 is flexible, and thus bends in response to an external force. The flexible tube section 13 is a tubular member extending from the operation section 2a.

Further, although not shown in FIG. 2, a monocular imaging section 30 is provided at the distal end section 11 of the insertion section 2b. The monocular imaging section 30 is an imaging device that has one imaging optical system, and that captures an image of an object as an image without parallax. That is, unlike a device using two optical systems with parallax such as a stereo optical system or the like, the monocular imaging section 30 is an imaging device that uses a single optical system to form an object into a single image, and captures the formed image by an imaging sensor. The image of the observation portion in the large intestine illuminated by the illumination light from the light source device 4 is captured by the imaging section 30. That is, the monocular imaging section 30 is provided at the distal end section 11 of the insertion section 2b and captures images inside the subject at a plurality of time points to acquire images at the plurality of time points. The position where the imaging section 30 is provided is not limited to the distal end section 11 of the insertion section 2b. For example, the imaging section 30 may be provided at a position closer to the base end than the distal end section 11 by guiding the light from the object.

The acquisition section 110 acquires an captured image of the object acquired by the monocular imaging section 30 provided at the insertion section 2b, which is inserted into the lumen, i.e., the object. Specifically, for example, the imaging signal obtained by the imaging section 30 is transmitted via signal lines in the universal cable 2c to an image processing device 3, which is described later with reference to FIG. 6, and the data of the captured image processed by the image processing device 3 is transmitted to the acquisition section 110. The acquisition section 110 may include an image processing module and may be configured to perform image processing based on imaging signals obtained by the imaging section 30. The acquisition section 110 may thus be implemented in various ways.

The actual size determination information acquisition section 112 is an interface for acquiring actual size determination information. The actual size determination information is information for determining the actual size of at least a portion of lumen. The actual size of at least a portion of a lumen refers to the actual size of the lumen as the object in the real space where the lumen exists, which is information based on data transmitted, for example, from a predetermined external sensor. The predetermined external sensor may be, for example, the magnetic sensor 16 described later with reference to FIG. 6; however, the predetermined external sensor may also be a position sensor or the like. Further, the actual size determination information acquisition section 112 may include an image processing module or the like, and may acquire actual size determination information by performing a process of determining the actual size based on the captured image of the object acquired by the imaging section 30. The details of the method for acquiring the actual size determination information are described later.

The lumen structure calculation section 120 calculates the three-dimensional structure of the lumen and the three-dimensional structure size information based on the actual size determination information and the captured image transmitted from the acquisition section 110. The three-dimensional structure of the lumen is a three-dimensional structure model of the lumen that is constructed in a virtual space based on captured two-dimensional images of the lumen. The lumen structure calculation section 120 forms a three-dimensional structure of the lumen based on the two-dimensional lumen images captured by the method described later. However, the size of the three-dimensional structure is a size in the virtual space where the three-dimensional structure model is constructed, and cannot be regarded as the actual size in the real space. Therefore, the lumen structure calculation section 120 of the present embodiment further calculates three-dimensional structure size information based on the captured image and the actual size determination information. The method for calculating the three-dimensional structure size information is specifically described later. Three-dimensional structure size information is information to determine the actual size of at least a portion of a three-dimensional structure; in other words, the three-dimensional structure size information is information obtained by converting the size of at least a portion of a three-dimensional structure in a virtual space into the actual size using the actual size determination information. More specifically, the actual size determination information mentioned above is information that associates a size in a virtual space with the actual size in the real space, i.e., information for converting a size in a virtual space to the actual size in the real space. The actual size determination information is sufficient enough if it is information by which the actual size of a specific portion 200, which is described later, can be determined; however, the actual size determination information may also be information by which actual size of a wider area than the region including the specific portion 200 can be determined. Further, although the specific portion 200 is, for example, a lesion, such as a cancer or polyp, the specific portion 200 is not limited to a lesion insofar as it is a site in the lumen that the surgeon desires to observe or to know the actual size thereof.

Based on the three-dimensional structure size information, the size estimation section 130 outputs specific portion size information representing the actual size of the specific portion 200 of the three-dimensional structure. For example, the size estimation section 130 outputs the size of the specific portion to the monitor 150 based on the three-dimensional structure size information transmitted from the lumen structure calculation section 120. The size estimation section 130 can be implemented by a display processor for enabling display of various images on the monitor 150 or a display module that operates on the display processor.

The respective sections of the lumen structure calculation system 100 are constituted of the following hardware. The respective sections of the lumen structure calculation system 100 refer to the acquisition section 110, the actual size determination information acquisition section 112, the lumen structure calculation section 120, and the size estimation section 130. The respective sections of the lumen structure calculation system 100 may include a specific portion setting section 140, which is described later with reference to FIG. 4, and may also include a feature point extraction section 122 and a three-dimensional position calculation section 124 described later with reference to FIG. 8. The hardware may include at least one of a circuit for processing digital signals and a circuit for processing analog signals. For example, the hardware may include one or a plurality of circuit devices or one or a plurality of circuit elements mounted on a circuit board. The one or a plurality of circuit devices is, for example, an integrated circuit (IC), FPGA (field-programmable gate array), or the like. The one or a plurality of circuit elements is, for example, a resistor, a capacitor, or the like.

Some or all of the sections of the lumen structure calculation system 100 may be implemented by the following processor. The lumen structure calculation system 100 includes a memory for storing information and a processor that operates based on the information stored in the memory. The information includes, for example, a program and various types of data. The processor includes hardware. The processor may be one of various processors including CPU (Central Processing Unit), a GPU (Graphics Processing Unit), a DSP (Digital Signal Processor), and the like. The memory may be a semiconductor memory such as an SRAM (Static Random Access Memory) or a DRAM (Dynamic Random Access Memory), or may be a register. The memory may also be a magnetic storage device such as a HDD (Hard Disk Drive), or an optical storage device such as an optical disc device. For example, the memory stores therein computer-readable commands, and part or all of the functions of the sections of the lumen structure calculation system 100 are achieved as processes with the processor executing the commands. These commands may be a command set included in a program, or may be commands to give operating instructions to the hardware circuit of the processor. Further, all or some of the sections of the lumen structure calculation system 100 may be implemented by cloud computing, and each process described later may be performed on the cloud computing.

Further, the respective sections of the lumen structure calculation system 100 of the present embodiment may be implemented as modules of a program that operates on the processor. For example, the acquisition section 110 is implemented as an image acquisition module. The lumen structure calculation section 120 is implemented as a module for acquiring information necessary for the calculation of lumen structure or a calculation module for performing calculation based on the information. The size estimation section 130 is implemented as a display process module.

The program that executes the processing performed by the sections of the lumen structure calculation system 100 of the present embodiment may be stored in an information storage device, which is, for example, a computer-readable medium. The information storage device can be implemented by, for example, an optical disc, a memory card, an HDD, a semiconductor memory, or the like. The semiconductor memory is, for example, a ROM. The lumen structure calculation system 100 performs various processes of the present embodiment based on a program stored in the information storage device. That is, the information storage device stores a program that causes a computer to function as each section of the lumen structure calculation system 100. The computer is a device including an input device, a processing section, a storage section, and an output section. Specifically, the program according to the present embodiment is a program that causes a computer to execute each of the steps described later with reference to FIG. 9, etc.

Figure 3:
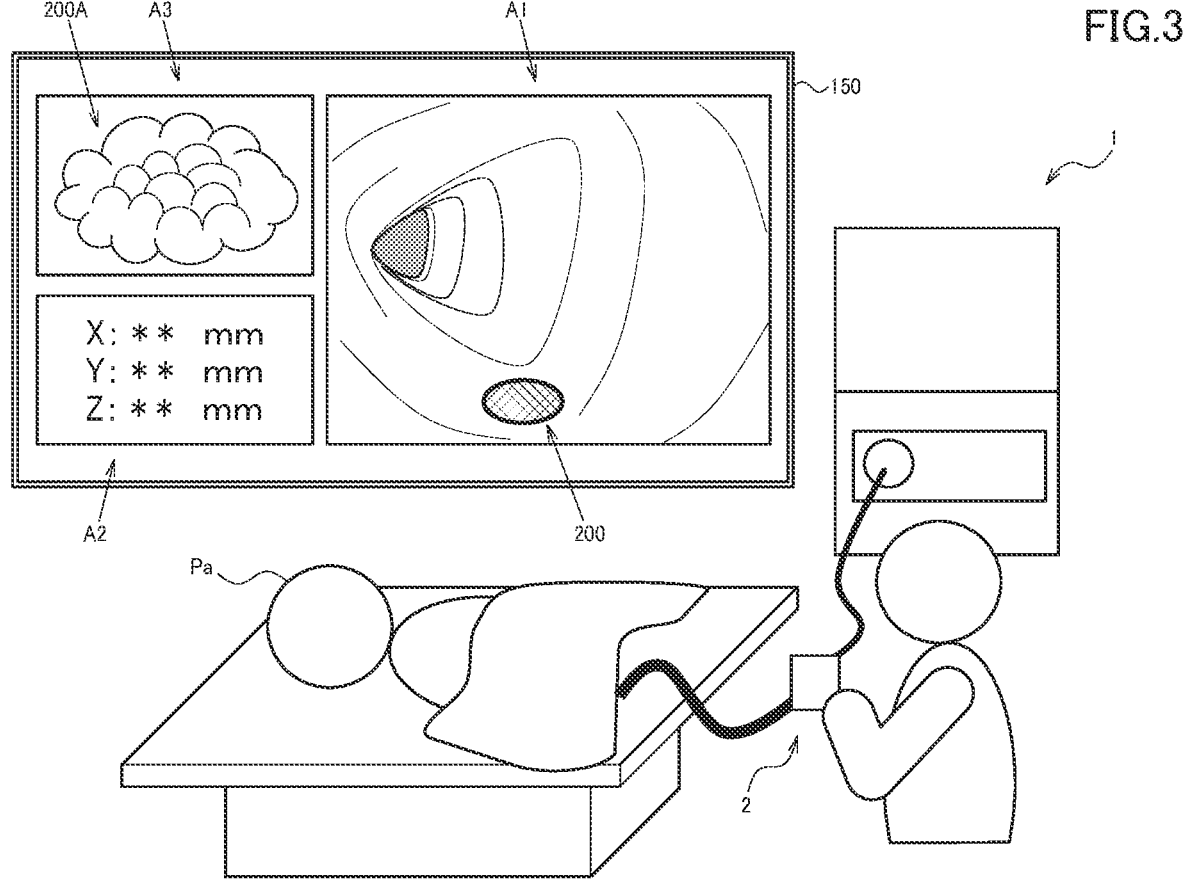
FIG. 3 illustrates an example of display of a monitor in which the method of the present embodiment is applied.

FIG. 3 illustrates an example of display of the monitor 150 in the case where the endoscope system 1 of the present embodiment is applied. The surgeon uses the endoscope system 1 to perform an endoscopy on the patient Pa, who is lying on his/her back on the bed, and the image captured by the endoscope 2 is displayed on the monitor 150. As shown in A1, a screen containing a lumen image captured by the imaging section 30 provided in the insertion section 2*b* is displayed on the monitor 150. As mentioned above, since the imaging section 30 is monocular, the surgeon can only capture the image of the lumen as a two-dimensional image. In addition, an image of the lumen close to the observer appears large and an image of the lumen far away from the observer appears small; therefore, it is difficult for the surgeon to accurately grasp the size of the specific portion 200. Therefore, the size of the specific portion 200 determined by the surgeon based on his/her impression by looking at the monitor 150 and the actual size of the specific portion 200 may greatly differ. In this regard, according to the present embodiment, the actual size of the specific portion 200 can be measured; therefore, it is possible to display a screen showing the actual size information of the specific portion 200, for example, as shown in A2.

It is also possible to allow the surgeon and the patient Pa to view the screen of the monitor 150 together. This allows the surgeon and the patient Pa to share detailed information about the specific portion 200. Further, it is possible that one kind of screen is displayed on a single monitor 150 while enabling the screen switchable depending on the content, or that a plurality of monitors 150 are provided to display separate images for each content. The display may thus be performed in various ways.

As described above, the endoscope system 1 of the present embodiment includes the insertion section 2*b*, the imaging section 30, the actual size determination information acquisition section 112, the lumen structure calculation section 120, and the size estimation section 130. The insertion section 2*b* is inserted into the lumen as the object. The imaging section 30 is monocular and is provided in the insertion section 2*b* to capture an image of the object. The actual size determination information acquisition section 112 acquires the actual size determination information, which is information for determining the actual size of at least a portion of a lumen. The lumen structure calculation section 120 calculates the three-dimensional structure of the lumen and the three-dimensional structure size information, which is information for determining the actual size of at least a portion of the three-dimensional structure, based on the captured image and the actual size determination information. Based on the three-dimensional structure size information, the size estimation section 130 outputs specific portion size information representing the actual size of the specific portion 200 of the three-dimensional structure. In this way, it is possible to measure the size of the specific portion 200 using an endoscope with a previously-known monocular imaging system. Since the imaging section 30 of the endoscope 2 is usually monocular, the imaging section 30 can only capture a two-dimensional image of the target observation portion. On the other hand, a double-eye type imaging section 30 has a large outer diameter, and therefore it can be used for very limited applications. Therefore, an endoscope system that further acquires three-dimensional information of the observation portion using a monocular optical system has not been proposed until now. In this regard, by applying the method of the present embodiment, the endoscope system 1 capable of measuring the size of the specific portion 200 can be used for a wider range of applications. In addition, since the measurement of the size of the specific portion 200 does not require empirical judgment by, for example, doctors, and also measurement of the lesion after the treatment will not be necessary, it is possible to reduce the burden on the doctors.

Further, the method of the present embodiment may also be realized as a lumen structure calculation system 100. Specifically, the lumen structure calculation system 100 of the present embodiment includes the acquisition section 110, the lumen structure calculation section 120, and the size estimation section 130. The acquisition section 110 acquires a captured image of the object acquired by the monocular imaging section 30 provided in the insertion section 2*b*, which is inserted into the lumen, i.e., the object, and the actual size determination information, which is information for determining the actual size of at least a portion of a lumen. The lumen structure calculation section 120 calculates the three-dimensional structure of the lumen and the three-dimensional structure size information, which is information for determining the actual size of at least a portion of the three-dimensional structure, based on the captured image and the actual size determination information. Based on the three-dimensional structure size information, the size estimation section 130 outputs specific portion size information representing the actual size of the specific portion 200 of the three-dimensional structure. In this way, the same effects as those described above can be achieved.

Further, the method of the present embodiment may also be realized as a method for creating lumen structure information. Specifically, the method for creating lumen structure information of the present embodiment includes acquiring a captured image of the object acquired by the monocular imaging section 30 provided in the insertion section 2*b*, which is inserted into the lumen, i.e., the object. Further, the method for creating lumen structure information of the present embodiment also includes acquiring actual size determination information, which is information to determine the actual size of at least a portion of the lumen. Further, the method for creating lumen structure information of the present embodiment also includes calculating the three-dimensional structure of the lumen and the three-dimensional structure size information, which is information for determining the actual size of at least a portion of the three-dimensional structure, based on the captured image and the actual size determination information. Further, the method for creating lumen structure information of the present embodiment also includes, based on the three-dimensional structure size information, outputting specific portion size information representing the actual size of the specific portion 200 of the three-dimensional structure. In this way, the same effects as those described above can be achieved.

Further, it is also possible to further output a specific portion structure 200A, which is a three-dimensional structural model of the specific portion 200, to the monitor 150, as shown in A3 in FIG. 3. That is, the size estimation section 130 performs a process of outputting the specific portion structure 200A based on the three-dimensional structure of the lumen and the specific portion size information. That is, in the endoscope system 1 of the present embodiment, the size estimation section 130 outputs the specific portion size information in association with information regarding the three-dimensional structure of the specific portion. In this way, the shape and the size of the specific portion 200 can be determined, thereby allowing the user to more accurately grasp the details of the specific portion 200. The user here is the surgeon; however, the user may include the patient Pa. For example, as shown in FIG. 3, both the surgeon operating the endoscope 2 and the patient Pa on the bed can view the information of the size of the specific portion 200 displayed on the monitor 150, thus allowing the surgeon and the patient Pa to accurately share the recognition regarding the specific portion 200.

In the description above, it was described that the actual size determination information is sufficient enough if it is information by which the actual size of the specific portion 200 can be determined; however, the actual size determination information may also provide the actual size of the entire three-dimensional structure of the lumen portion captured by the imaging section 30. That is, the lumen structure calculation section 120 of the endoscope system 1 of the present embodiment calculates three-dimensional structure information with the actual size based on the actual size determination information. This enables determination of the actual size of the three-dimensional structure of the entire lumen, thus enabling more detailed understanding of the situation regarding the specific portion 200. For example, the size of the lesion, i.e., the specific portion 200, can be compared with the size of the observed lumen portion, thereby allowing the surgeon to more accurately grasp the severity of the lesion. In this case, the size estimation section 130 performs a process of extracting a predetermined region including the specific portion structure 200A from the three-dimensional structure of the lumen, and outputs the predetermined region and the specific portion size information to the monitor 150, thereby performing the display shown in A2 and A3 in FIG. 3.

Figure 4:
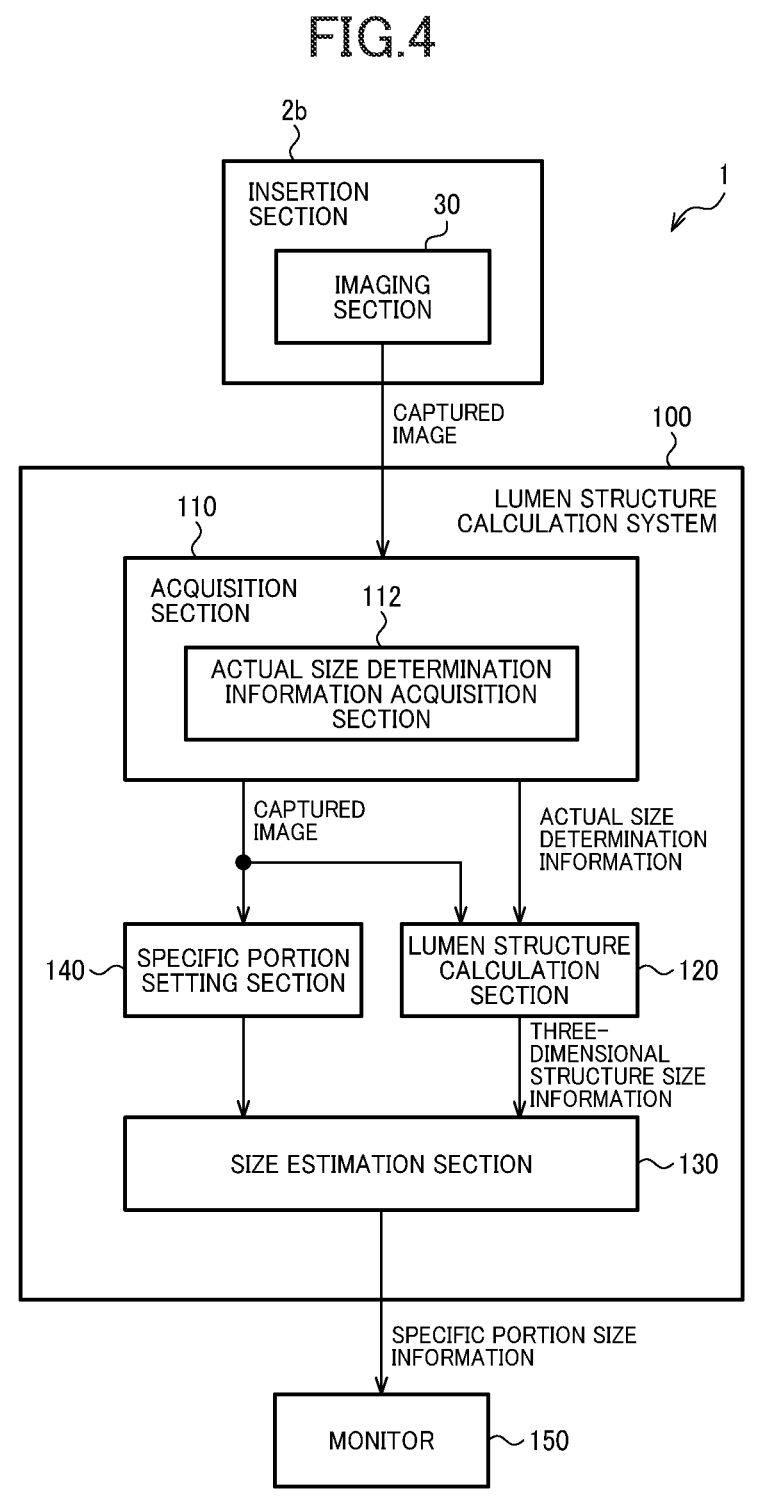

Further, the configuration of the endoscope system 1 of the present embodiment is not limited to that shown in FIG. 1. For example, the endoscope system 1 of the present embodiment may further include a specific portion setting section 140, as shown in FIG. 4. That is, the specific portion setting section 140 of the endoscope system 1 of the present embodiment sets the specific portion 200 based on the captured image transmitted from the acquisition section 110. The specific portion setting section 140 can be implemented by a processor or an image processing module, as with the acquisition section 110, the actual size determination information acquisition section 112, the lumen structure calculation section 120, and the size estimation section 130.

Figure 5:
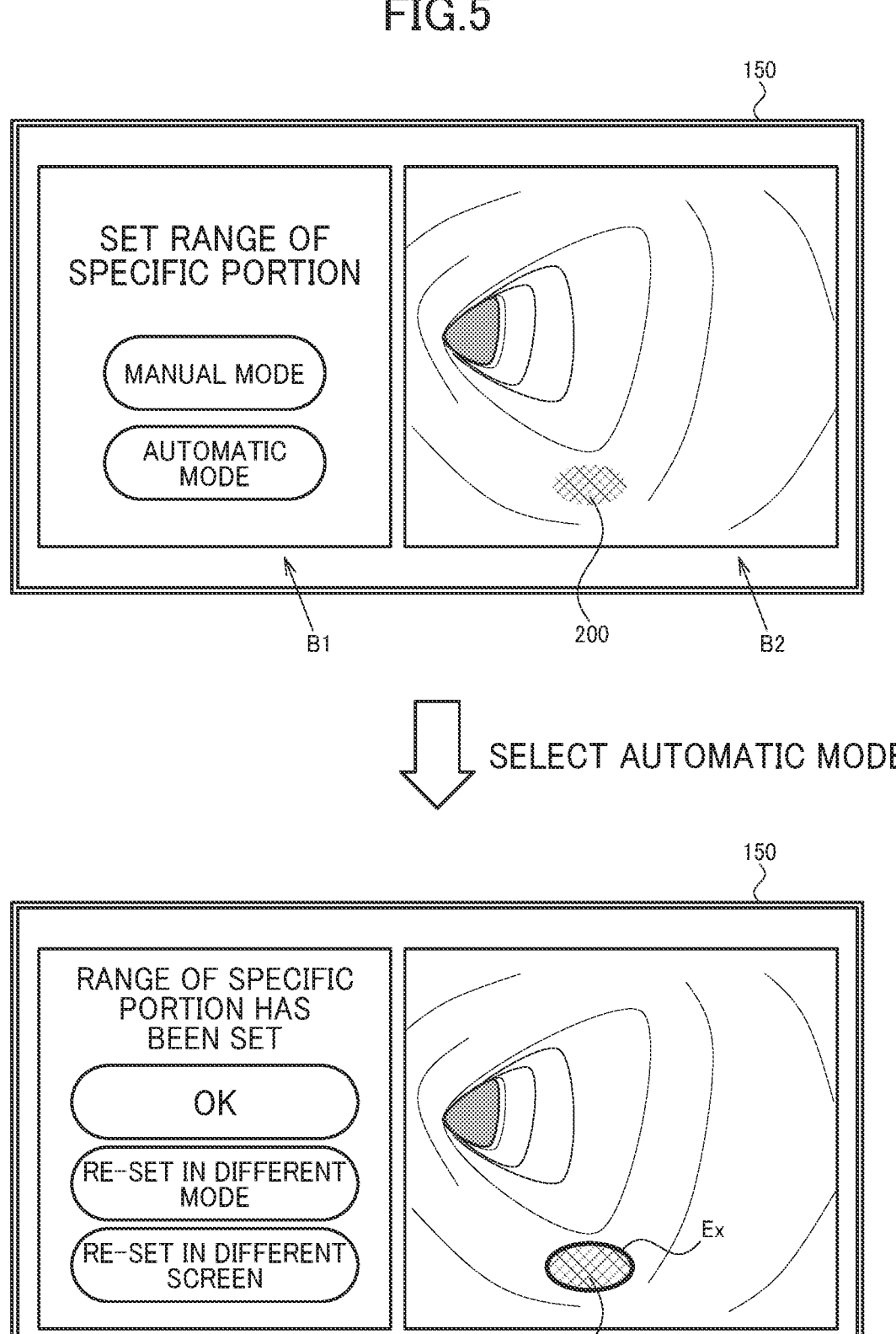
FIG. 5 illustrates an example of display of a monitor to describe a specific portion range setting section.

FIG. 5 illustrates an example of display of the monitor 150 to describe the specific portion setting section 140. For example, if the surgeon finds a portion that looks like a lesion from the captured image when he/she performs endoscopy on the patient Pa, the surgeon performs a selection enabling setting of the range of the specific portion 200 on the screen shown in B1 in the monitor 150. Specifically, for example, the surgeon performs a selection as to whether the specific portion 200 is set by a manual mode or by an automatic mode. In the endoscope system 1 of the present embodiment, the specific portion setting section 140 has a first setting mode and a second setting mode. The second setting mode uses a different method of setting the specific portion 200 from that of the first setting mode. The surgeon selects one of the plurality of setting modes that use different methods of setting the specific portion 200. As described above, in the endoscope system 1 of the present embodiment, the specific portion setting section 140 enables selection of setting mode from among a plurality of setting modes. In this way, the specific portion 200 can be appropriately set. There may be a plurality of modes for each of the manual mode and the automatic mode.

For example, when the specific portion 200 is displayed on the screen shown in B2, and if the surgeon selects the automatic mode, a specific portion range display Ex that surrounds the specific portion 200 is displayed, for example, as shown in B3. For example, the specific portion setting section 140 generates information that specifies the range of a lesion, i.e., the specific portion 200, and transmits it to the size estimation section 130. The size estimation section 130 then displays the information on the monitor 150, thus performing the display shown in B3. That is, in the endoscope system 1 of the present embodiment, the specific portion setting section 140 presents the specific portion on the captured image in a manner visible to a user. The user is, for example, the surgeon. In this way, the boundary between the specific portion 200 and regions other than the specific portion 200 is clarified, and the size of the specific portion 200 can thus be clarified.

The setting of the specific portion 200 by the manual mode is performed, for example, by an input operation by the surgeon via an input section (not shown), thereby displaying the specific portion range display Ex. That is, in the manual mode, the specific portion range display Ex is set by each surgeon by empirically determining the boundary between the specific portion 200 and regions other than the specific portion 200 based on the color, brightness, smoothness, shape, and the like of the lumen being observed. On the other hand, in the setting of the specific portion 200 by the automatic mode, for example, the boundary between the specific portion 200 and regions other than the specific portion 200 is determined through an inference process based on instructions from a trained model including a program describing an inference algorithm and parameters used for the inference algorithm. This enables the specific portion setting section 140 to automatically generate information of the specific portion range display Ex, thereby enabling automatic display of the specific portion range display Ex on the monitor 150 by the size estimation section 130. That is, the specific portion setting section 140 includes a memory (not shown) storing the trained model. When the surgeon selects the automatic mode, the trained model is read out from the memory.

The trained model is generated by a training device (not shown) that is present outside the endoscope system 1. However, the training device may be included in the endoscope system 1. In the training phase, the trained model is updated for each disease case, for example, by inputting captured image including the specific portion 200 and the data of the specific portion range display Ex determined by the manual mode into the training device.

Further, for example, a neural network may be used as the inference algorithm. The weight coefficients of the inter-node connections in the neural network correspond to the parameters. The neural network includes an input layer to which image data is entered, an intermediate layer for performing a calculation process with respect to the data input via the input layer, and an output layer for outputting recognition results based on the calculation result output from the intermediate layer. Although a convolutional neural network (CNN) is preferable as a neural network for image recognition process, other neural network technologies may also be employed. Further, the inference algorithm is not limited to a neural network, and various types of machine learning techniques for use in image recognition may be used. Since these technologies have been known, descriptions thereof are omitted.

Based on the above, in the endoscope system 1 of the present embodiment, the specific portion setting section 140 has a classifier that automatically sets the specific portion 200. In this way, the range of the specific portion 200 is automatically set without the surgeon's determination, thereby reducing the error in setting the specific portion range display Ex. In addition, since the surgeon's determination is not necessary, the burden on the surgeon can be reduced.

Further, in the present embodiment, if the captured image contains a plurality of items of color information, the plural items of color information may be separated into a first color information and a second color information, which is different from the first color information, and the first color information and the second color information may be used as parameters for the inference algorithm. More specifically, for example, if it is known that the color of the lumen is close to red and that the lesion, i.e., the specific portion 200, is close to blue, blue is used as the first color information as a parameter to infer the region of the specific portion 200. Similarly, red is used as the second color information as a parameter to infer the regions other than the specific portion 200. That is, in the endoscope system 1 of the present embodiment, the captured image can be separated into a plurality of items of color information, and the specific portion setting section 140 sets the specific portion using the first color information included in the plural items of color information. In this way, the boundary between the specific portion 200 and regions other than the specific portion 200 can be inferred more accurately, thereby more accurately displaying the specific portion range display Ex in the automatic mode.

Further, when the specific portion range display Ex is displayed, as shown in B4, the display indicating that the range of the specific portion 200 has been set is performed and also the display to ask the surgeon to confirm whether the specific portion range display Ex is appropriately displayed is performed. If the surgeon determines, for example, that the specific portion range display Ex is appropriately displayed, he/she performs an input operation for the confirmation. Further, if the surgeon determines that the specific portion range display Ex is not appropriately displayed, the surgeon may choose to re-set the range of the specific portion 200. The case in which the specific portion range display Ex is not appropriately displayed is, for example, the case in which the region indicated by the specific portion range display Ex is displayed in a position significantly different from the region of the specific portion 200 visually identified by the surgeon on the monitor 150. The surgeon can, for example, set the range of the specific portion 200 again for the same image in a different setting mode. This is because, in some cases, the specific portion 200 can only be set by the manual mode, for example, due to incompletion in machine learning. That is, after setting the specific portion 200 in a captured image in the first setting mode, the specific portion setting section 140 can re-set the specific portion 200 in the second setting mode for the same captured image for which the specific portion 200 has been set in the first setting mode. Further, the surgeon may also choose to re-set the range of the specific portion 200 using a different image. This is because if the appearance of the display of the specific portion 200 changes as a result of re-capturing of the image, the result of setting of the specific portion 200 by the automatic mode may change. Specifically, when the first captured image is a captured image for which the specific portion 200 is set in the first setting mode, the specific portion setting section 140 can redo the setting of the specific portion 200 using a second captured image that is different from the first captured image. The second captured image is a captured image including the same specific portion 200 as that in the first captured image. As described above, in the endoscope system 1 of the present embodiment, the specific portion setting section 140 can redo the setting of the specific portion 200 in a different setting mode of the same image or using a different image. In this way, the range of the specific portion 200 can be more appropriately set.

Figure 6:
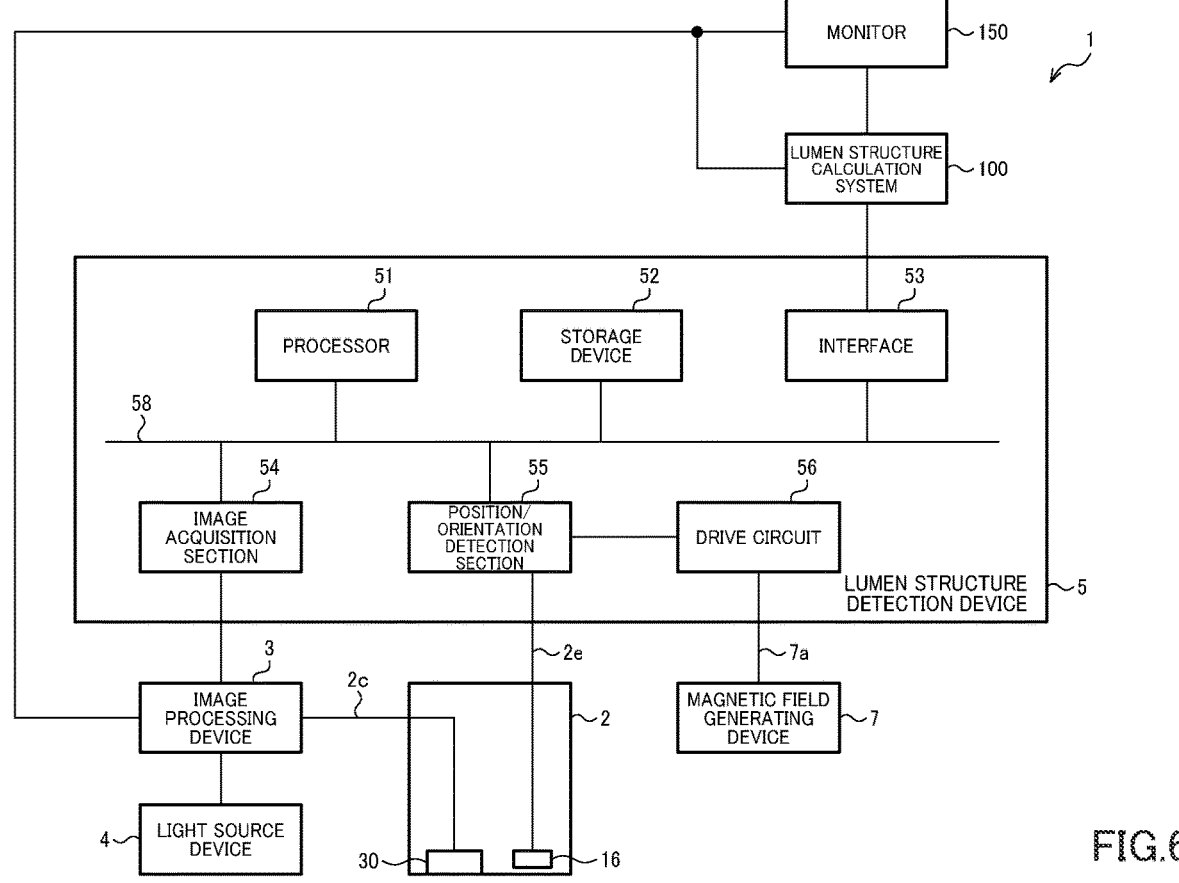
FIG. 6 is a block diagram explaining another configuration example of an endoscope system.

The configuration of the endoscope system 1 of the present embodiment is not limited to the one shown above. For example, as shown in FIG. 6, the endoscope system 1 may have a configuration that further includes an image processing device 3, a light source device 4, a lumen structure detection device 5, a magnetic sensor 16, and a magnetic field generating device 7.

The image processing device 3 is a video processor to perform predetermined image processing with respect to the received imaging signals and generate captured images. The video signals of the generated captured image are output from the image processing device 3 to the monitor 150, and a live captured image is displayed on the monitor 150. This allows, for example, the surgeon to observe the inside of the large intestine of the patient Pa when the distal end section 11 of the insertion section 2*b* is inserted through the anus of the patient Pa.

Figure 7:
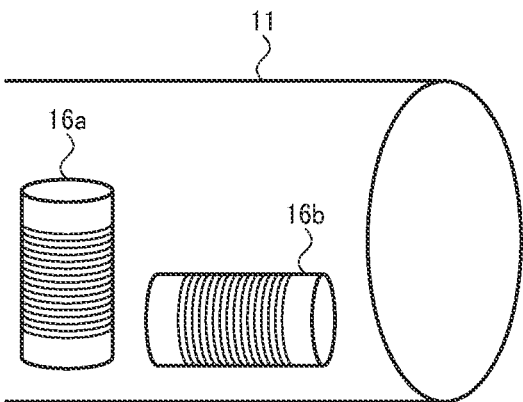
FIG. 7 is an explanatory view of a magnetic sensor.

A magnetic sensor 16 is disposed in the distal end section 11 of the insertion section 2*b*. Specifically, the magnetic sensor 16 is a detection device disposed in the vicinity of the imaging section 30 of the distal end section 11 to detect the position and orientation of the point-of-view of the imaging section 30. The magnetic sensor 16 has two coils 16*a* and 16*b*, for example, as shown in FIG. 7. The two central axes of the two cylindrical coils 16*a* and 16*b* are orthogonal to each other. Thus, the magnetic sensor 16 is a 6-axis sensor that detects the position coordinates and the orientation of the distal end section 11. The orientation herein refers to the Euler angle. The magnetic sensor 16 is not limited to the example shown in FIG. 7, and may be implemented in various different ways, such as by changing the combination and arrangement of the coils 16a and 16b. For example, if it is desired to prioritize the prevention of increase in the diameter of the insertion section 2b, the angle at which the two coils 16a and 16b intersect may be changed, although this may limit the performance and the number of detectable axes. Further, for example, the magnetic sensor 16 may be constituted of a single coil 16a. A signal line 2e of the magnetic sensor 16 extends from the endoscope 2 and is connected to the lumen structure detection device 5.

The magnetic field generating device 7 generates a predetermined magnetic field, and the magnetic sensor 16 detects the magnetic field generated by the magnetic field generating device 7. The magnetic field generating device 7 is connected to the lumen structure detection device 5 by a signal line 7a. The magnetic field detection signal is supplied from the endoscope 2 via the signal line 2e to the lumen structure detection device 5. Instead of the magnetic sensor 16, a magnetic field generating element may be provided in the distal end section 11, and instead of the magnetic field generating device 7, the magnetic sensor 16 may be provided outside the patient Pa to detect the position and orientation of the distal end section 11. Herein, the magnetic sensor 16 detects, in real time, the position and orientation of the distal end section 11, in other words, the position and orientation of the point-of-view of the image captured by the imaging section 30.

The light source device 4 is a light source device capable of emitting normal light for a normal light observation mode. In the case where the endoscope system 1 also has a special light observation mode in addition to the normal light observation mode, the light source device 4 selectively emits normal light for the normal light observation mode and special light for the special light observation mode. The light source device 4 emits either normal light or special light as the illumination light depending on the state of a changeover switch for switching the observation mode provided in the image processing device 3.

The lumen structure detection device 5 includes a processor 51, a storage device 52, an interface 53, an image capturing section 54, a position/orientation detection section 55, and a drive circuit 56. The sections of the lumen structure detection device 5 are connected to each other by a bus 58.

The processor 51 is a control section having a CPU and a memory. The processor 51 controls processing of each section in the lumen structure detection device 5. The memory is a storage section including ROM, RAM, and the like. The ROM stores various processing programs to be executed by the CPU, as well as various types of data. The CPU is capable of reading out and executing various programs stored in the ROM and the storage device 52.

The storage device 52 stores a lumen structure calculation program. The lumen structure calculation program is a software program that calculates the lumen structure information from the information of position and orientation of the distal end section 11 and the captured images. When the CPU reads out and executes the lumen structure calculation program, the processor 51 constitutes a lumen structure calculation section that calculates the three-dimensional structure of the lumen based on the image captured by the imaging section 30 and the three-dimensional arrangement of the distal end section 11 detected by the magnetic sensor 16.

The interface 53 outputs the lumen structure information calculated by the processor 51 to the lumen structure calculation system 100. The interface 53 is, for example, a communication interface that performs communication with the lumen structure calculation system 100.

The image capturing section 54 is a processing section that captures an image obtained in the image processing device 3 at a certain period. For example, thirty captured images per second, which is equal to the frame rate, are acquired from the image processing device 3 through the endoscope 2. Although the image capturing section 54 herein captures the thirty captured images per second, it is also possible to capture the images at a period longer than the frame rate. For example, the image capturing section 54 may capture, for example, three images per second.

The position/orientation detection section 55 controls the drive circuit 56 that drives the magnetic field generating device 7 to enable the magnetic field generating device 7 to generate a predetermined magnetic field. The position/orientation detection section 55 detects the generated magnetic field with the magnetic sensor 16, and generates data of the position coordinates (x, y, z) and the orientation (vx, vy, vz) of the imaging section 30 from the detected magnetic field detection signal. The orientation refers to the Euler angle. That is, the position/orientation detection section 55 is a detection device that detects the position and orientation of the imaging section 30 based on the detection signal from the magnetic sensor 16. More specifically, the position/orientation detection section 25 detects three-dimensional arrangement time-based change information, which is information of changes in three-dimensional arrangement over time. Therefore, the position/orientation detection section 25 acquires the three-dimensional arrangement information of the insertion section 2b at a plurality of time points.

Figure 8:
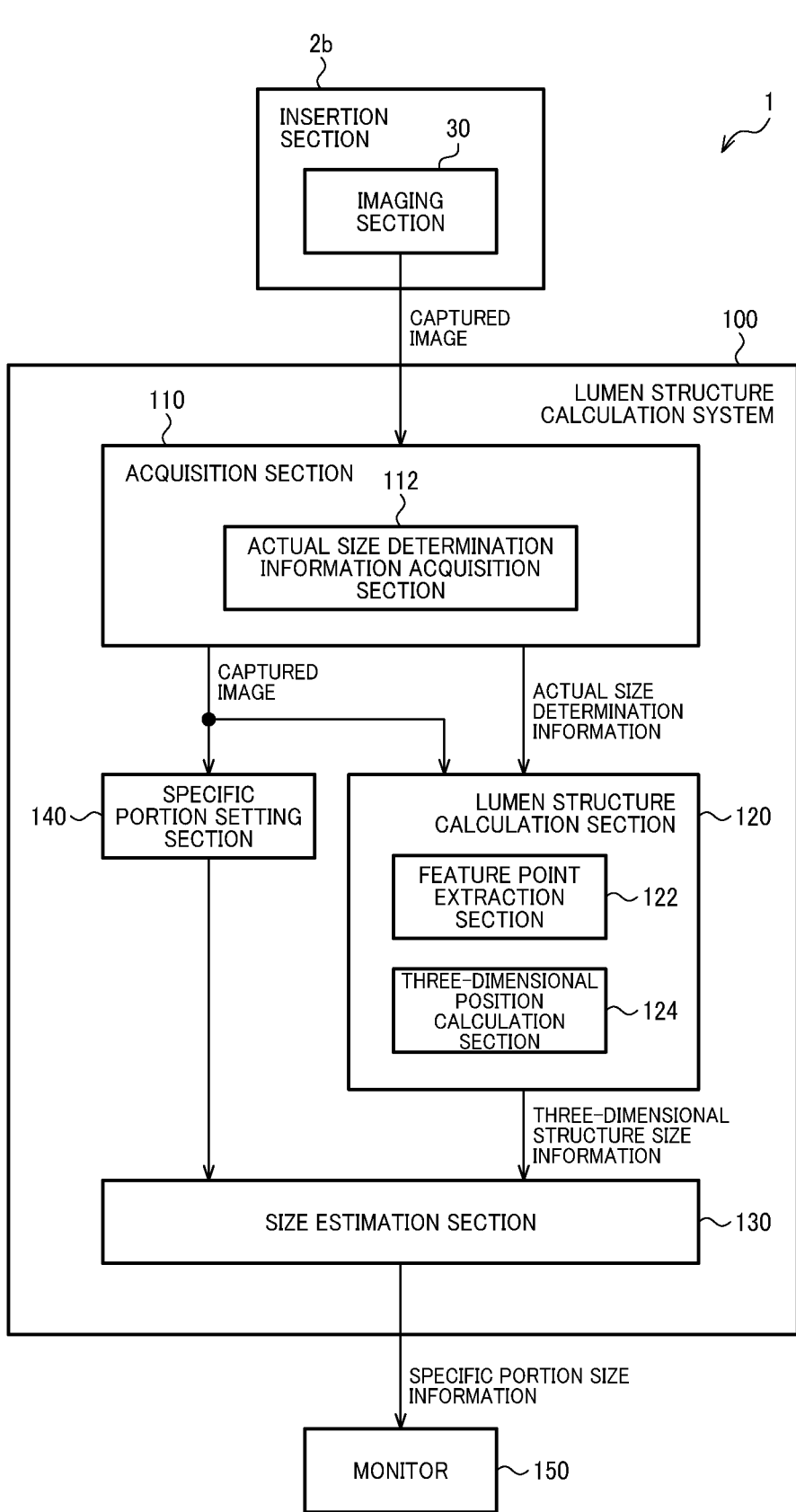
FIG. 8 is a block diagram explaining another configuration example of an endoscope system.

Although the above description is an example in which the three-dimensional structure of the lumen is calculated by the lumen structure detection device 5, which is an external device of the lumen structure calculation system 100, the method of the present embodiment is not limited to this, and the three-dimensional structure of the lumen may be calculated by the lumen structure calculation system 100. FIG. 8 is a block diagram of another configuration example of the endoscope system 1. In the endoscope system 1 in FIG. 8, the lumen structure calculation section 120 includes a feature point extraction section 122 that extracts a plurality of feature points F in each captured image, and a three-dimensional position calculation section 124 that calculates the position of each feature point F in a three-dimensional space based on the positions of the plurality of feature points F in the captured image. The feature point extraction section 122 and the three-dimensional position calculation section 124 can be implemented by a processor equivalent to the processor 51 in FIG. 6 and a program module that operates on the processor 51. In FIG. 8, illustration of the image processing device 3, the light source device 4, the magnetic field generating device 7, etc. are omitted.

Next, a method for calculating a lumen structure is described with reference to FIG. 9, FIG. 10, FIG. 11, and FIG. 12. Although the following description describes a method performed by the sections of the endoscope system 1 shown in FIG. 6, the method may also be realized by the endoscope system 1 shown in FIG. 8. For example, in the following description, each of the processes in the flow-charts of FIG. 9 and FIG. 11 are realized by the processor 51; however, these processes can also be realized by processors constituting the lumen structure calculation section 120, the feature point extraction section 122, the three-dimensional position calculation section 124, and the like, as necessary.

Figure 9:
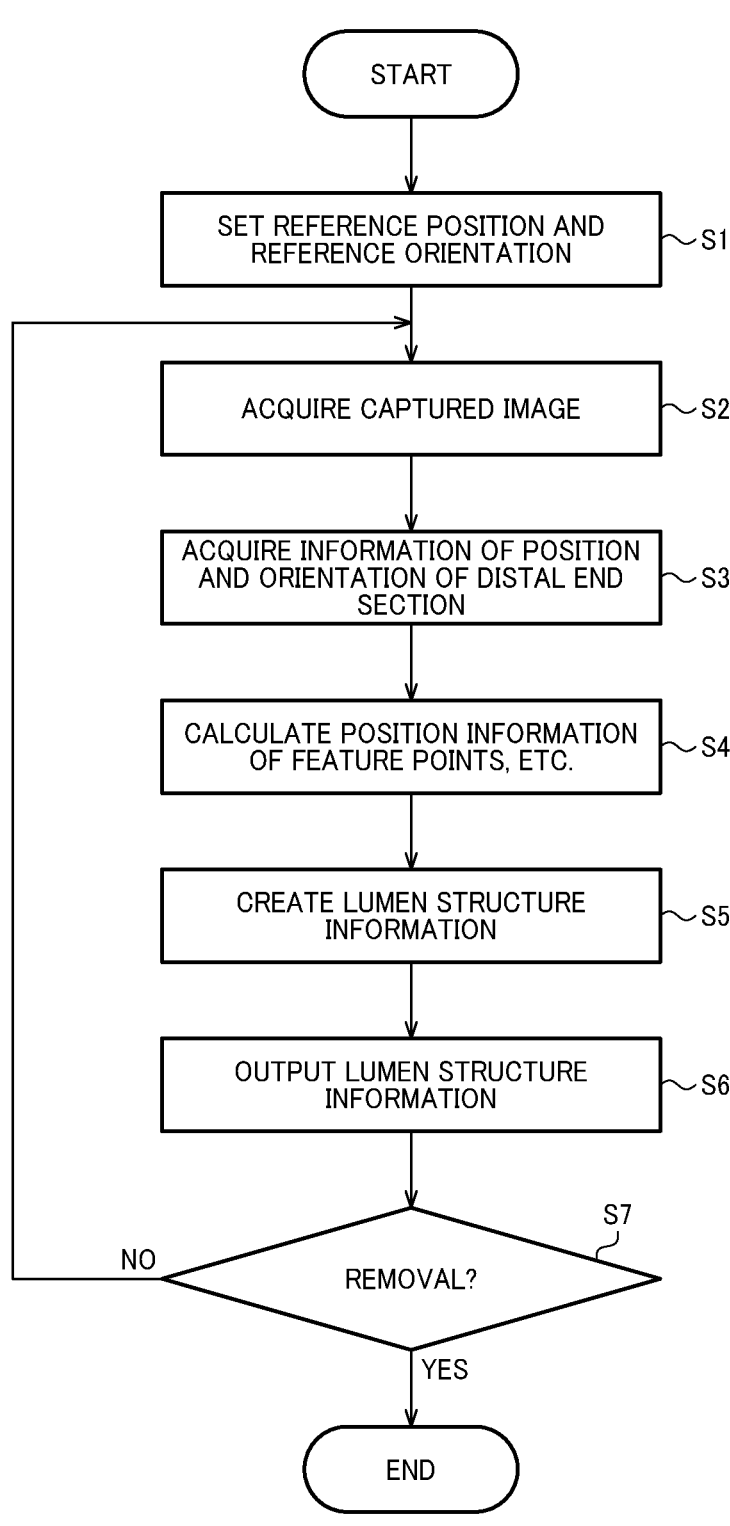
FIG. 9 is a flowchart explaining a process example of acquisition of lumen structure information.

FIG. 9 is a flowchart of an example of a flow of a lumen structure calculation process. First, the surgeon performs a predetermined operation with respect to an input device (not shown) with the distal end section 11 of the insertion section 2*b* disposed at a predetermined position. The predetermined position is, for example, the anus shown in C1 when the lumen is the large intestine, as in FIG. 10. Based on this operation, the processor 51 sets position and orientation data from the position/orientation detection section 55 as the reference position and the reference orientation of the distal end section 11 when calculating the lumen structure (step S1). For example, with the distal end section 11 placed on the predetermined position, the surgeon sets the reference position and the reference orientation of the distal end section 11 at the predetermined position in the three-dimensional space as the initial value. The lumen structure calculated in the process below is calculated based on the reference position and the reference orientation set herein.

After setting the reference position and the reference orientation, the surgeon inserts the distal end section 11 to a specified position. The specified position is, for example, the innermost part of the large intestine shown in C2 in FIG. 10. In the state where the distal end section 11 of the insertion section 2*b* is disposed at the specified position shown in C2, the surgeon sends air to expand the large intestine and pulls the insertion section 2*b* to move the insertion section 2*b* toward the predetermined position shown in C1, and observe the inner wall of the large intestine by curving the curving section 12 in various directions while, for example, stopping pulling the insertion section 2*b* on the way. The lumen structure of the large intestine is calculated while the surgeon is observing the inner wall of the large intestine.

The image capturing section 54 acquires captured images at every predetermined period $\Delta t$ from the captured images supplied every $\frac{1}{30}$ second from the image processing device 3 (step S2). The period $\Delta t$ is, for example, 0.5 seconds. The CPU acquires information of the position and orientation of the distal end section 11 output by the position/orientation detection section 55 upon the acquisition of the captured image (step S3).

The processor 51 calculates the position information of a plurality of feature points F, etc. in the three-dimensional space, in an image acquired in the step S2 and one or more previously-acquired images (step S4). The set of the position information of a plurality of feature points F, etc. determined by the calculation corresponds to the information of lumen structure. As described below, the position information of each feature point F may be calculated from the image information using SLAM (Simultaneous Localization and Mapping), SfM (Structure from Motion), or like methods, or using the triangulation principles. The method for calculating the position of each feature point F is described later.

When the first image is acquired, since there are no previously-acquired images, the process of the step S4 is not performed until a predetermined number of images are acquired.

The processor 51 creates or updates the lumen structure information by adding the calculated position information of the plurality of feature points F, etc. (step S5).

Figure 10:
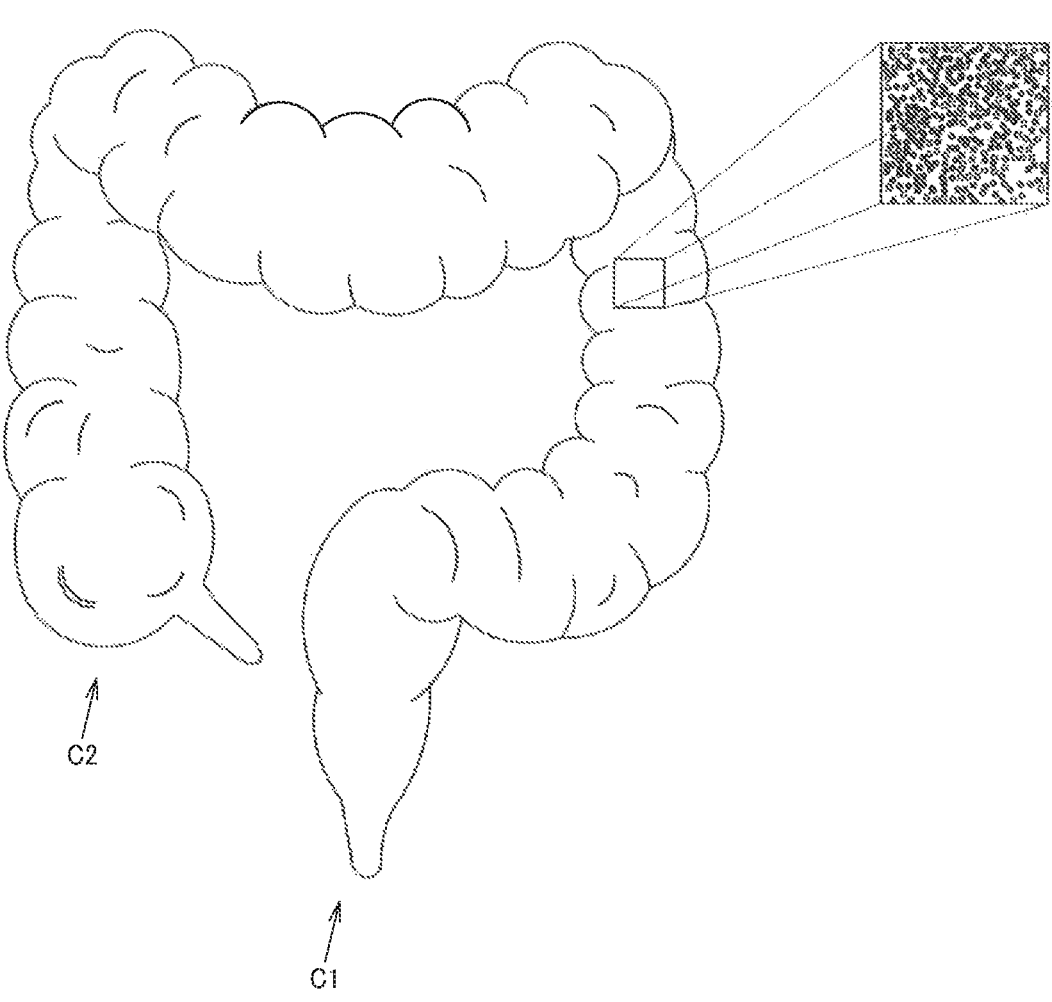
FIG. 10 is an explanatory view of an example of lumen structure information.
Figure 11:
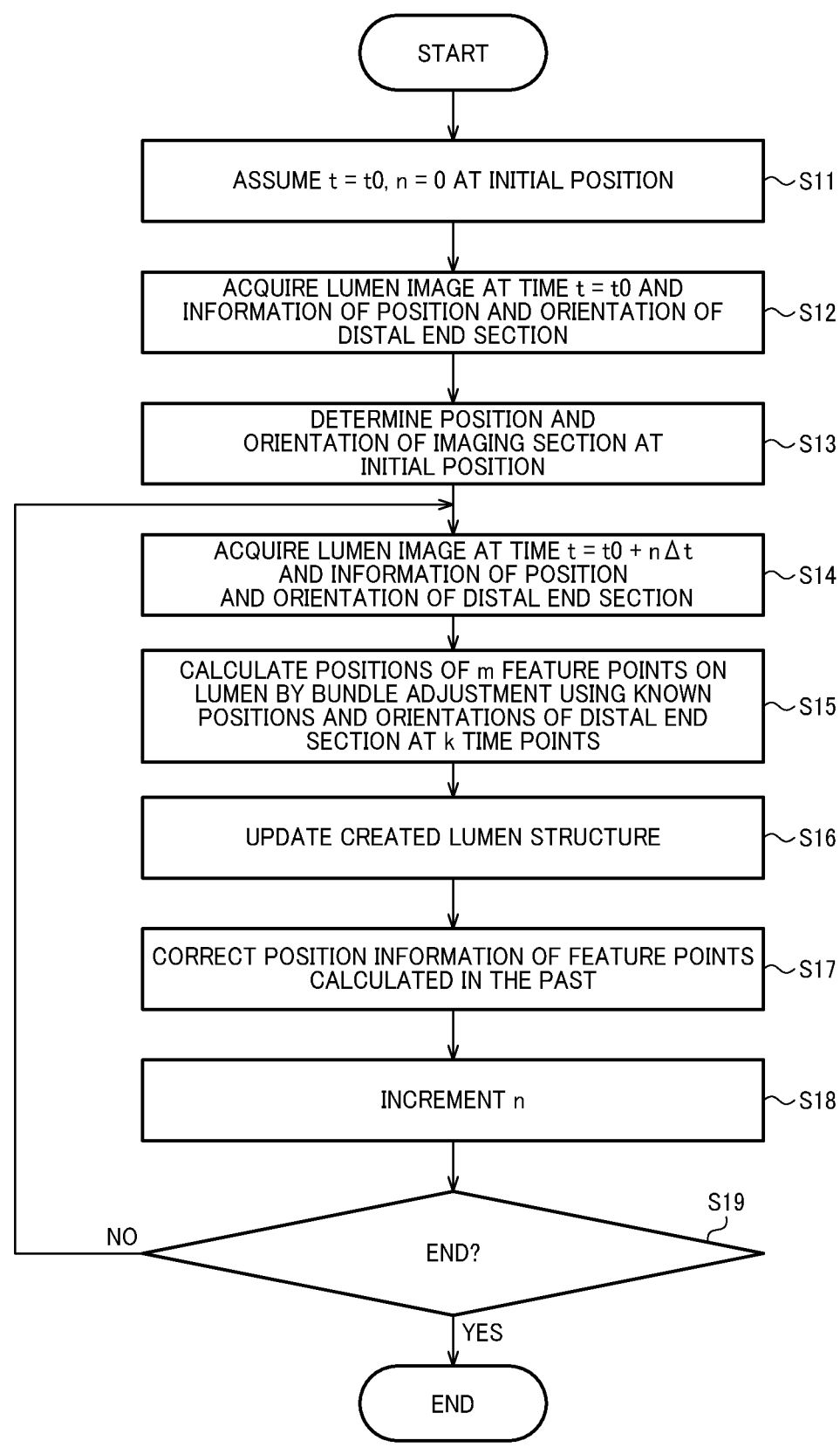
FIG. 11 is a flowchart explaining another process example of acquisition of lumen structure information.

As shown in FIG. 10, the set of one or more feature points F or the like in the region observed by the endoscope 2 constitutes the lumen structure information created in the step S5. The lumen structure information is 3D data. FIG. 10 illustrates an image of the lumen structure information viewed from a given point-of-view. For example, when the lumen structure information is displayed, the user can input instructions to change the point-of-view position, thereby viewing the lumen structure from a desired direction among 360 degree.

Further, although FIG. 10 shows an example of the lumen structure information that even takes into account the unevenness in the lumen, the lumen structure information may be information that is more simplified. For example, the lumen structure information may be a cylinder model. By assuming that the lumen has a cylindrical shape, the processing load can be reduced. For example, when a sensor, such as the magnetic sensor 16, is not used, the effect of reducing the amount of calculation when assuming a cylindrical lumen becomes more significant. For simplification, it is also possible to assume a straight lumen with no bends or only simple bends, or assume a structural model with differences from a standard lumen structure only in size, such as the length and the diameter for each part or the like.

The interface 53 of the lumen structure detection device 5 outputs the generated lumen structure information to the lumen structure calculation system 100 (step S6). Further, in the step S6, the interface 53 may also control the display of the lumen structure information on the monitor 150. Next, the processor 51 determines whether or not the insertion section 2*b* has been removed from the patient (step S7). For example, when the insertion section 2*b* has been removed, the user performs user input indicating the end of observation using an input device (not shown). The processor 51 performs the determination shown in S7 based on the user input. If the removal has not been done (No in the step S7), the process returns to the step S2.

As described above, the lumen structure calculation section 120 calculates the three-dimensional structure of the lumen from the calculated position of each feature point F in the three-dimensional space. In this way, a three-dimensional structure based on captured image can be generated.

There are various methods for calculating the position of the feature point F, etc. in the step S4. Several methods are described below. The processor 51 may use SLAM, SfM, or similar methods to calculate the positions of the feature points F on a plurality of consecutive images.

In the generation of the lumen structure information, it is possible to apply a bundle adjustment that optimizes the internal parameter, external parameter and world coordinate point group from images using a nonlinear least squares method. For example, using each of the presumed parameters, the world coordinate points of the plurality of feature points F thus extracted are subjected to perspective projective transformation, thereby obtaining each parameter and each world coordinate point group with minimum reprojection error.

The external parameters for the distal end section 11 are calculated by solving the 5-point and 8-point algorithms. The position of the feature point F is calculated according to the position of the distal end section 11 using the triangulation method. The error E between the coordinates of the 3D point projected on the image plane and the feature point F due to the reprojection error is expressed by the following equation (1).

[Math. 1]

$$E = \sum_{i=1}^{K} \sum_{j=1}^{L} \|P_i - P_{sj}\|^2 \tag{1}$$

wherein L is the number of the feature points F on K images, Psj is the coordinate position of the 3D point Pi presumed by the parameter of the distal end section 11 with triangulation on the image plane, and Pi is the coordinate position of the corresponding feature point F on the image. The position coordinates of the distal end section 11 is calculated using the LM (Levenberg-Marquardt) method so that the function of the error E in the equation (1) is minimized.

In the descriptions of FIG. 4 and FIG. 5, it was described that when the captured image contains a plurality of items of color information, the plural items of color information may be separated into the first color information and the second color information, which is different from the first color information. However, it is also possible to add a process of separating the image information into the first color information and the second color information to the flowchart in FIG. 9. Further, it is also possible to perform the step S3 onward based on the separated second color information. The same applies to the flowchart in FIG. 11. Specifically, in the endoscope system 1 of the present embodiment, the lumen structure calculation section 120 outputs the three-dimensional structure and the three-dimensional structure size information using the second color information that is included in the plural items of color information and that does not include the first color information. In this way, the accuracy in the estimation of the three-dimensional structure can be improved because the three-dimensional structure, etc. is generated based on an image having a color similar to that of the lumen, which is the observation object.

FIG. 11 is a flowchart of a method of performing the calculation of the position of each feature point F in the three-dimensional space using a bundle adjustment. When the predetermined position mentioned above is set as the initial position, the processor 51 sets the time t to t0, and sets the software counter value n to 0 (step S11).

The processor 51 acquires a captured image at the time t0 and the information of position and orientation of the distal end section 11 (step S12). The captured image is acquired from the image processing device 3. The information of position and orientation of the distal end section 11 is acquired from the position/orientation detection section 55. The processor 51 determines the position and orientation of the distal end section 11 at the initial position (step S13). For example, the predetermined position (x, y, z) is determined to be (0,0,0) and the orientation (vx, vy, vz) is determined to be (0,1,0). The step S11 and the step S13 correspond to the step S1 in FIG. 9.

The processor 51 acquires a captured image at the time (t0+nΔt) and the information of position and orientation of the distal end section 11 (step S14). The step S12 and the step S14 correspond to the step S2 in FIG. 9. The information of the position and orientation of the distal end section 11 may be modified. For example, using the Kalman filter, the path in which the distal end section 11 passes in the past is modified, and the position of the distal end section 11 in the past is modified based on the modified path.

When n becomes k, the processor 51 extracts a plurality of feature points F in each captured image, and calculates the positions of m feature points F contained in the obtained captured image by bundle adjustment described above using the known positions and orientations of the distal end section 11, i.e., the known three-dimensional arrangements of the distal end section 11, at k time points (step S15). Therefore, the process of extracting a plurality of feature points F in each endoscope image in the step S15 constitutes the feature point extraction section that extracts a plurality of feature points F in each captured image. In the step S15, the feature points F that commonly appear in the captured images at the plurality of time points are extracted. The process of calculating the position of each feature point F in the three-dimensional space in the step S15 constitutes the three-dimensional position calculation section that calculates the positions of the feature points F in the three-dimensional space from the positions of the extracted plurality of feature points F in the captured image and the three-dimensional arrangement of the insertion section 2b. More specifically, the positions of the feature points F in the three-dimensional space are calculated based on the three-dimensional arrangement information of the insertion section 2b at the plurality of time points and positions on the captured image of the feature points F that commonly appear in the captured images at the plurality of time points. Then, the position of each feature point F in the three-dimensional space is determined by bundle adjustment.

Based on the above, in the endoscope system 1 of the present embodiment, the feature point extraction section 122 extracts feature points that commonly appear in captured images at a plurality of time points. Further, the three-dimensional position calculation section 124 acquires the three-dimensional arrangement information of the insertion section 2b at a plurality of time points based on the output of the magnetic sensor 16, which is a position sensor that extracts information of at least a portion of the position and orientation of the imaging section 30. Further, the three-dimensional position calculation section 124 calculates the positions of the feature points F in the three-dimensional space based on the three-dimensional arrangement information of the insertion section 2b at a plurality of time points and the positions of the feature points F on the captured image that commonly appear in the captured images at the plurality of time points.

Figure 12:
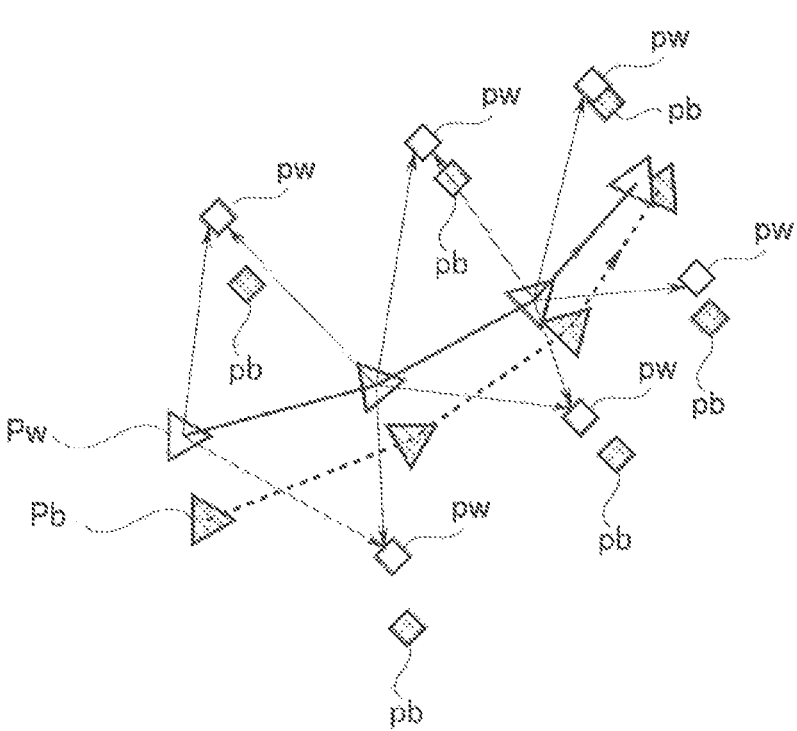
FIG. 12 is a schematic diagram explaining relationship between a plurality of feature points and position and orientation of a distal end section.

FIG. 12 is a schematic diagram illustrating the relationship between the feature points F on a plurality of captured images consecutively acquired and the position and orientation of the distal end section 11. In FIG. 12, white triangle Pw represents the actual position and orientation of the distal end section 11, and the black triangle Pb represents the presumed position and orientation of the distal end section 11. It is shown that the distal end section 11 actually moved along the solid line. The presumed distal end section 11 moved along the dotted line. As the time passed, the position of the distal end section 11 moved and the orientation of the distal end section 11 changed.

Further, in FIG. 12, the white rectangle pw represents the actual position of the feature point F, and the black rectangle pb represents the presumed position, i.e., the calculated position of the feature point F. The feature point F is, for example, a location in the captured image with a characteristic shape or color and thus is easy to identify or track.

To obtain the three-dimensional lumen structure of the large intestine, the coordinates of a plurality of feature points F on the inner wall of the intestinal tract of the large intestine are determined, and a three-dimensional model is generated by the set of the plurality of coordinates thus determined or by connecting the coordinates. That is, the three-dimensional structure of the lumen is determined from the calculated position of each feature point F in the three-dimensional space.

In FIG. 12, since the information of the position and orientation of the distal end section 11 at each time point contains information of 6 axes, the information of the position and orientation of the distal end section 11 at k time points contains 6 k pieces of information. Since the position of each feature point F contains information of 3 axes, the information of the positions of m feature points F contains 3 m pieces of information. Accordingly, when using SLAM, SfM, or similar methods, the number of parameters to be determined is (6 k+3 m).

In the method of the present embodiment, as described above, the magnetic sensor 16 is provided in the distal end section 11 of the endoscope 2, and the lumen structure detection device 5 may include the position/orientation detection section 55 that acquires the position and orientation information detected by the magnetic sensor 16. In this case, the 6 k parameters corresponding to the positions and orientations of the distal end section 11 are known parameters. Since the optimization calculation by the processor 51 is limited to the calculation of 3 m parameters, it is possible to reduce the amount of processing for the optimization calculation. Therefore, the processing can be accelerated. Further, the reduction in the number of parameters also suppresses the accumulation of detection errors, thereby preventing an increase in error in the position of the generated three-dimensional model.

Further, even if the distal end section 11 of the insertion section 2b of the endoscope 2 is pressed against the inner wall of the lumen or immersed in dirty cleaning water, or even if appropriate consecutive captured images cannot be obtained due to blurred image or the like, the information of the position and orientation of the distal end section 11 can be obtained. Therefore, even if consecutive images were not successfully obtained in some cases, the calculation of the 3 m parameters is likely to succeed. As a result, the robustness of the calculation of the lumen structure increases.

The explanation continues below with reference back to FIG. 11. The processor 51 updates the lumen structure information by adding the newly calculated position information of the feature point F to the lumen structure information already created (step S16). The step S16 corresponds to the step S5 in FIG. 9.

The processor 51 modifies position information of the feature points F calculated in the past (step S17). Among the 3 m feature points F obtained by the new calculation, the position information of feature points F calculated in the past is modified using the position information newly calculated, for example, by the calculation of average value. The process in the step S17 does not have to be performed; instead, the position information of each feature point F calculated in the past may be updated by the newly calculated position information of the feature point F.

After the step S17, the processor 51 increments n by 1 (step S18) and determines whether or not a command of end of inspection has been entered (step S19). The command of end of inspection is, for example, a predetermined command that is input to the input device by the surgeon, for example, after the insertion section 2b has been removed from the large intestine. When the command is entered (YES in the step S19), the process ends.

If the command of end of inspection is not entered (NO in the step S19), the process goes to the step S14. As a result, the processor 51 acquires a captured image after period Δt from the last acquisition time of captured image (step S14), and executes the processes in the step S15 onward.

By performing these processes, the lumen structure information is output. However, in the lumen structure information obtained by these methods, the positional relationship between the respective feature points F is determined in a relative manner; therefore, the information of absolute size value cannot be obtained.

In the present embodiment, the method of setting the specific portion range display Ex described in FIGS. 4 and 5 may be combined with the method of calculating the lumen structure described in FIGS. 9 to 12. Specifically, this enables, based on the captured image, extraction of the feature points F by the process of calculating the lumen structure in addition to the setting of the range of the specific portion 200; therefore, the feature points F within the range of the specific portion 200 are also extracted. Further, since the position of each feature point F in the three-dimensional structure of the lumen is calculated, the positions of the feature points F inside the specific portion 200 are also calculated. In other words, the position of the specific portion 200 is calculated by associating the extracted feature points F in the specific portion 200 with the feature points F in the three-dimensional structure. As described above, the endoscope system 1 of the present embodiment further includes a specific portion setting section 140 that extracts the specific portion 200 from the captured image and that also extracts the feature points F from the captured image including the specific portion 200. The specific portion setting section 140 associates the extracted feature points F with the feature points F in the three-dimensional structure to set the position of the specific portion 200 in the three-dimensional structure.

Figure 13:
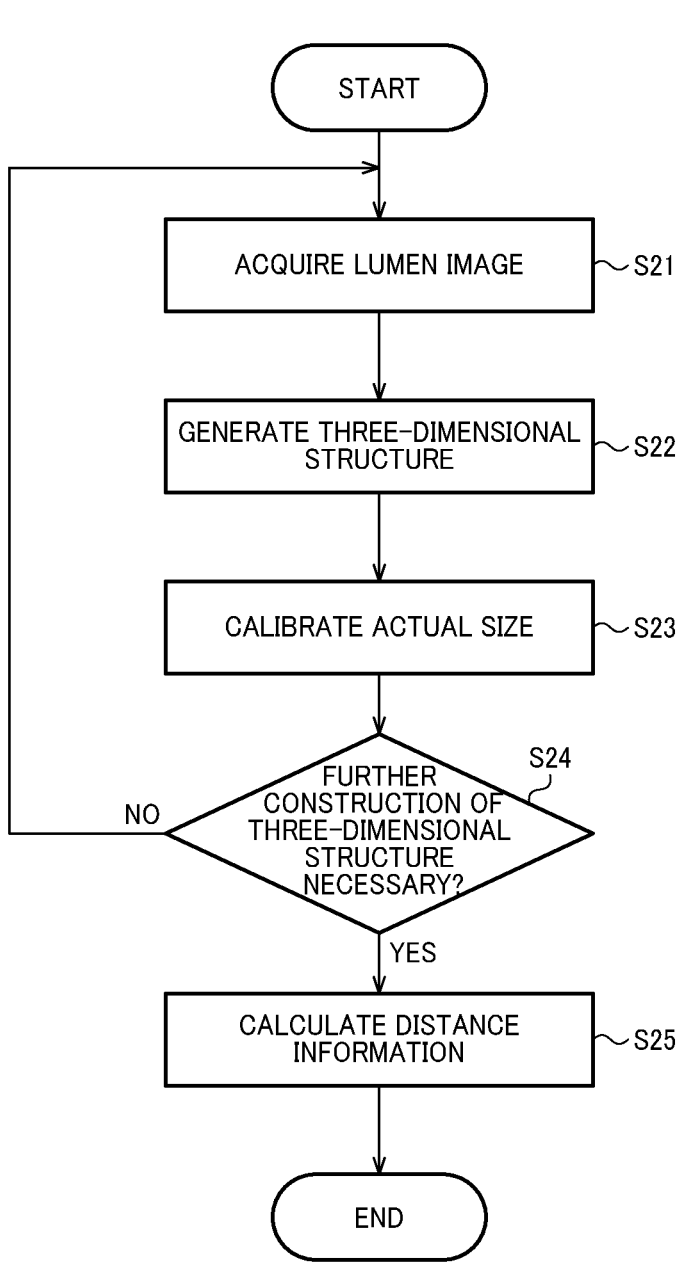
FIG. 13 is a flowchart explaining a process example of calculation of three-dimensional structure size information.

Next, the method for calculating three-dimensional structure size information is described below. FIG. 13 is a flowchart explaining a process example of calculation of three-dimensional structure size information. The lumen structure calculation system 100 acquires a lumen image (step S21). Specifically, for example, the acquisition section 110 acquires a captured image transmitted from the image processing device 3. Thereafter, the lumen structure calculation system 100 generates a three-dimensional structure (step S22). Specifically, the position information of a plurality of feature points F, etc. in the three-dimensional space is calculated using any of the methods described above with reference to FIGS. 9 to 12, thereby generating a three-dimensional structure of the lumen.

Figure 14:
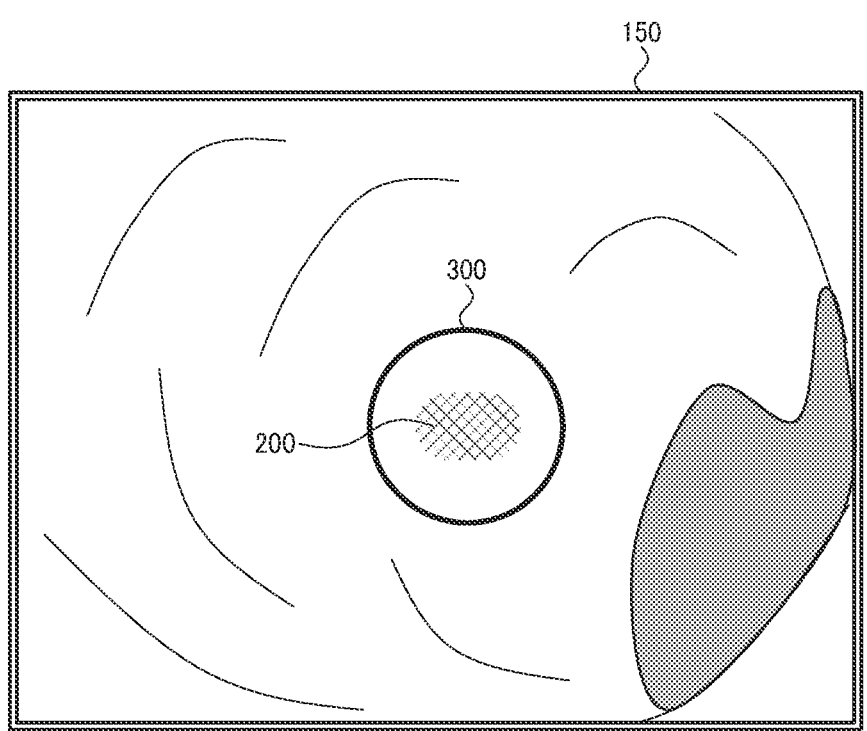
FIG. 14 illustrates an example of display of a monitor to describe an object for comparison.

Next, the lumen structure calculation system 100 calibrates the actual size (step S23). Specifically, for example, an object for comparison for which at least a portion of size information is known in advance is placed in the image capturing range. The object for comparison used herein is, for example, a treatment tool to be inserted into the lumen through the distal end section 11 to be used for observation, diagnosis, treatment, or the like; however, the object for comparison may also be such as a cap attached to the distal end section 11 as long as at least a portion thereof appears in the field of view upon the image capturing. For example, as shown in FIG. 14, in the case where an O-ring 300 is placed around the specific portion 200, which is a lesion, the O-ring 300 may be the object for comparison. The method for placing the O-ring 300 is not limited to the example shown in FIG. 14. For example, the O-ring 300 may be placed in the vicinity of the specific portion 200 without surrounding the specific portion 200. The size of the O-ring 300 may be smaller than the size of the specific portion 200. In this case, the lumen image in the step S21 described above includes an image of the O-ring 300, and the three-dimensional structure in the step S22 includes the three-dimensional structure of the O-ring 300. In other words, the actual size determination information acquisition section 112 acquires the known actual size of the O-ring 300 as actual size determination information based on the captured image of the lumen, and the lumen structure calculation section 120 performs a process of calibrating the actual size of the three-dimensional structure generated in the step S22 based on the actual size determination information. The process of the step S23 by the lumen structure calculation system 100 may be performed by the surgeon by pressing a treatment tool or the like having, for example, a wire-like, knife-like, or rod-like shape, against the inner wall of the lumen. This is because, as mentioned above, it is sufficient that at least the size of the object for comparison to be placed around the specific portion 200 is known. As described above, the actual size determination information acquisition section of the endoscope system 1 of the present embodiment acquires a size on the captured image of an object for comparison, which appears in the captured image and has a known size, as the actual size determination information. In this way, the absolute size value of the three-dimensional structure can be grasped.

Thereafter, the lumen structure calculation system 100 determines whether or not further construction of the three-dimensional structure is necessary, and if it is necessary, (YES in the step S24), the process returns to the step S21; if it is not necessary (NO in the step S24), distance information is calculated (step S25). For example, if the surgeon finds a lesion, i.e., the specific portion 200, the three-dimensional structure of the lumen will continue to be constructed because observation will continue until the surgeon determines that the image of the lesion has been optimally captured. If the surgeon determines that the image of the lesion has been optimally captured, calculation of the specific portion 200 is performed by the method described above in FIG. 5.

The process loop from the step S21 to the step S23 is preferably performed within a predetermined period. The same applies to the process loop of the steps S31, S32, S33, S34, and S35 described later with reference to FIG. 15. For example, the large intestine as the target of image capturing periodically deforms due to peristaltic, pendulum, or segmental movements, and the predetermined period is a time period from the start of deformation to the next deformation. This is because if the large intestine, etc. is deformed before the completion of the processes of the steps S21 to S23, construction of an appropriate three-dimensional structure fails. Specifically, in the endoscope system 1 of the present embodiment, the lumen structure calculation section 120 outputs a three-dimensional structure and three-dimensional structure size information based on captured images captured within a predetermined time and actual size determination information acquired within a predetermined time. In this way, the three-dimensional structure of the lumen can be appropriately formed. Further, if the deformation occurs after a three-dimensional structure containing absolute size value is obtained, the state of deformation can be followed in the observation object.

Figure 15:
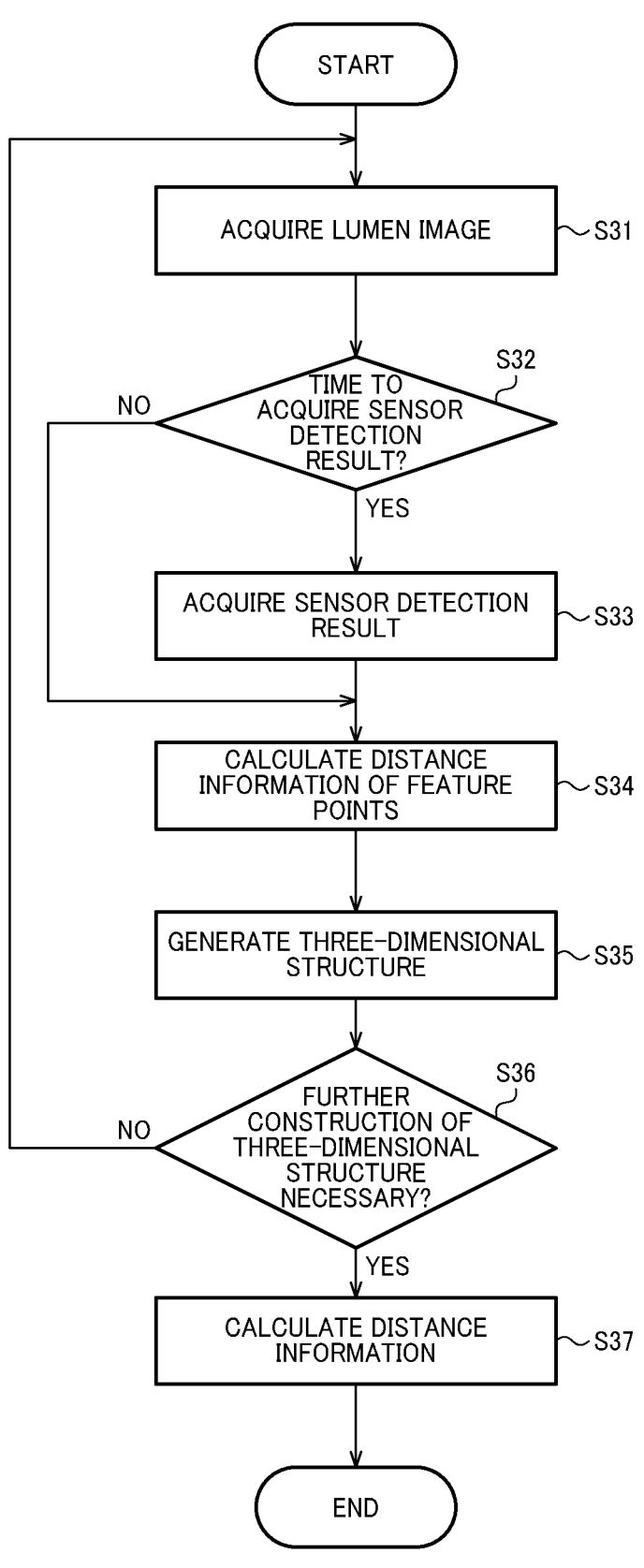
FIG. 15 is a flowchart explaining another process example of calculation of three-dimensional structure size information.

FIG. 15 is a flowchart explaining another process example of calculation of three-dimensional structure size information. The process example of FIG. 15 is an example of a process of acquiring captured image and absolute value size information to determine a three-dimensional structure containing absolute value size. The lumen structure calculation system 100 acquires a lumen image as in the step S21 in FIG. 13 (step S31). Thereafter, the lumen structure calculation system 100 performs a process of determining whether or not it is the time to acquire the detection results of the sensor, and if it is the time to acquire the detection results of the sensor (YES in the step S32), the detection results of the sensor are acquired (step S33). The details of the process in the step S33 are described later. After the process in the step S33 described above is performed, or if it is not the time to acquire the detection results of the sensor (NO in the step S32), the lumen structure calculation system 100 calculates the distance between the feature points F (step S34). Then, the lumen structure calculation system 100 generates a three-dimensional structure by the same method as in the step S22 in FIG. 13 (step S35). The process example in FIG.

15 differs from the process example in FIG. 13 in that the generated three-dimensional structure contains absolute value size information at the time of step S35. Thereafter, as in the steps S24 and S25 in FIG. 13, the lumen structure calculation system 100 determines whether or not further construction of the three-dimensional structure is necessary, and if it is necessary, (YES in the step S36), the process returns to the step S31; if it is not necessary (NO in the step S36), distance information is calculated (step S37).

Next, the details of the step S33 in FIG. 15 are described below. The sensor in the step S33 is, for example, the magnetic sensor 16, which is a position sensor. In the step S33, specifically, for example, the lumen structure calculation section 120 acquires, based on output information from the magnetic sensor 16, which is a position sensor, information regarding the position and orientation of the distal end section 11, which is actual size determination information, in other words, information regarding the position or orientation of the imaging section 30, through the actual size determination information acquisition section 112. Then, in the step S34, the lumen structure calculation section 120 generates a three-dimensional structure of the lumen including the actual size by incorporating the information regarding the position or orientation of the imaging section 30 into the feature points F extracted from the lumen image acquired in the step S31. That is, the actual size determination information acquisition section 112 acquires information regarding the output of the magnetic sensor 16, which is a position sensor that extracts information of at least a portion of the information regarding the position and orientation of the imaging section 30, as the actual size determination information. In this way, absolute size information can be added to the three-dimensional structure that can be obtained only in a relative manner.

Further, in addition to the magnetic sensor 16, the position and orientation of the distal end section 11 may be detected using a shape sensor and an insertion amount/torsion amount sensor. The shape sensor, which is not shown in the figure, is a fiber sensor serving as a bending sensor that detects the amount of bending from the curvature of a specific point using, for example, optical fibers. The insertion amount/torsion amount sensor, which is also omitted from the figure, has a cylindrical shape with a hole through which the insertion section 2b can be inserted, and an encoder for detecting the insertion amount of the insertion section 2b in the axial direction and an encoder for detecting the rotation amount of the insertion section 2b around the axis are provided on the inner circumference of the hole. By using the shape sensor and the insertion amount/torsion amount sensor, the surgeon can assume the position and orientation of the distal end section 11 based on the initial position, and the insertion amount and the torsion amount of the insertion section 2b.

Figure 16:
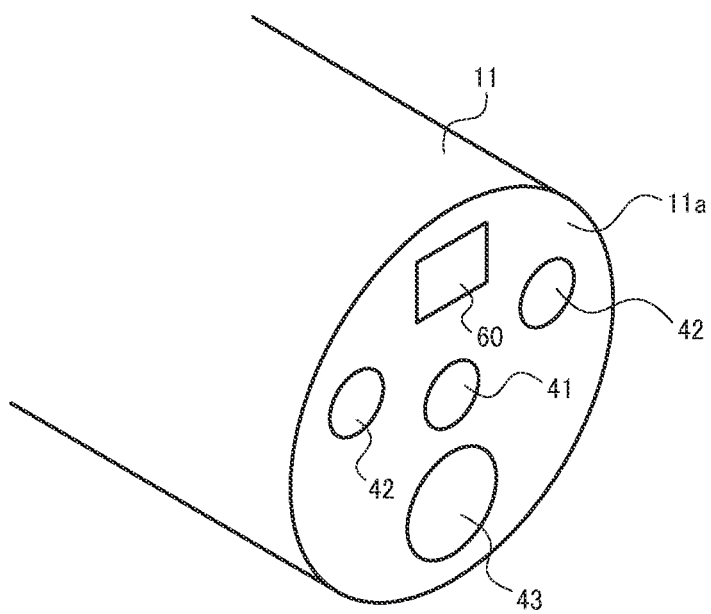
FIG. 16 is an explanatory view of a TOF sensor.

Further, the sensor in the step S33 may be, for example, a distance measuring sensor. FIG. 16 is a perspective view of the distal end portion of the distal end section 11 of the insertion section 2b with a distance measuring sensor. On a distal end surface 11a1 of the distal end section 11, an observation window 41, two lighting windows 42, a forceps opening 43, and a TOF (Time Of Flight) sensor 60, which is a distance measuring sensor, are provided. The TOF sensor 60 measures the time of flight of light to detect a distance image to measure the distance. The TOF function is embedded in each pixel of the image sensor. Therefore, the TOF sensor 60 obtains distance information for each pixel. That is, the TOF sensor 60 is provided in the distal end section 11 of the insertion section 2b and detects the distance from the distal end section 11 to the inner wall of the lumen. This enables acquisition of information of the distance from the imaging section 30 to the object. The distance information is, for example, information of distance distribution; however, the distance information may also be information of distance with respect to a single point. Then, in the step S33, the lumen structure calculation section 120 acquires, via the actual size determination information acquisition section 112, information of the distance from the distal end section 11 to the inner wall of the lumen, which is the target of image capturing, as actual size determination information from the TOF sensor 60. Then, in the step S34, the lumen structure calculation section 120 generates a three-dimensional structure of the lumen containing the actual size by incorporating the information of the distance from the distal end section 11 to the inner wall of the lumen into the feature points F extracted from the lumen image acquired in the step S31. The distance measuring sensor is not limited to the TOF sensor 60, and may also be a sensor of other methods, such as LiDAR (Light Detection and Ranging/Laser Imaging Detection and Ranging). As described above, the actual size determination information acquisition section 112 of the endoscope system 1 of the present embodiment acquires information regarding the output of the TOF sensor 60, which is a distance measurement section to extract information of the distance from the imaging section 30 to the object, as the actual size determination information.

The method for determining the distance distribution from the imaging section 30 to the object is not limited to the method using a sensor. For example, the distance distribution from the imaging section 30 to the object may be obtained by presuming the steric shape of the lumen from a single captured image by the Shape From Shading method. The Shape From Shading method is a method for determining the three-dimensional shape of an article based on its surface shading. For example, in a lumen, by solving a partial differential equation describing a curve on the surface of inner wall at an equal distance from the lighting window 42, the three-dimensional shape can be calculated. Since this is a known technique, the detailed explanation thereof is omitted.

Figure 17:
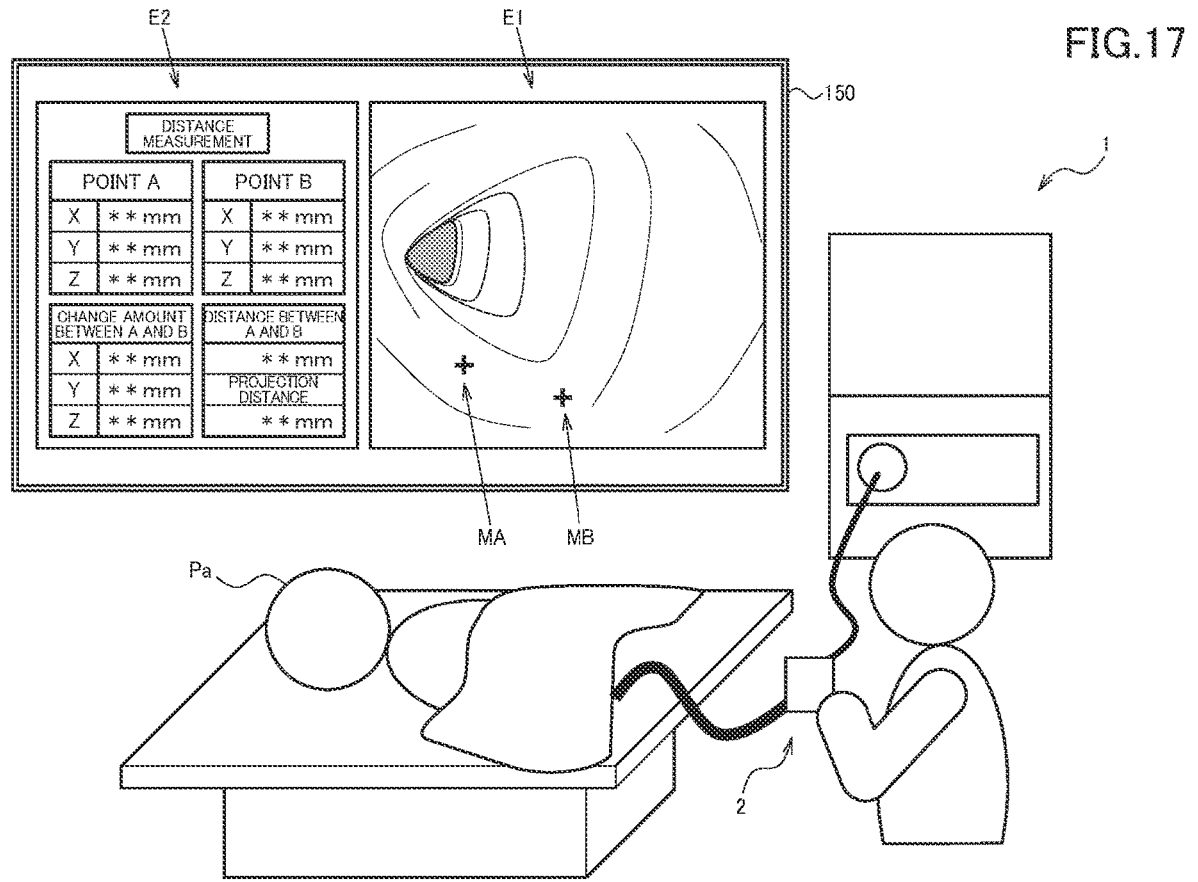
FIG. 17 illustrates another example of display of a monitor in which the method of the present embodiment is applied.
Figure 18:
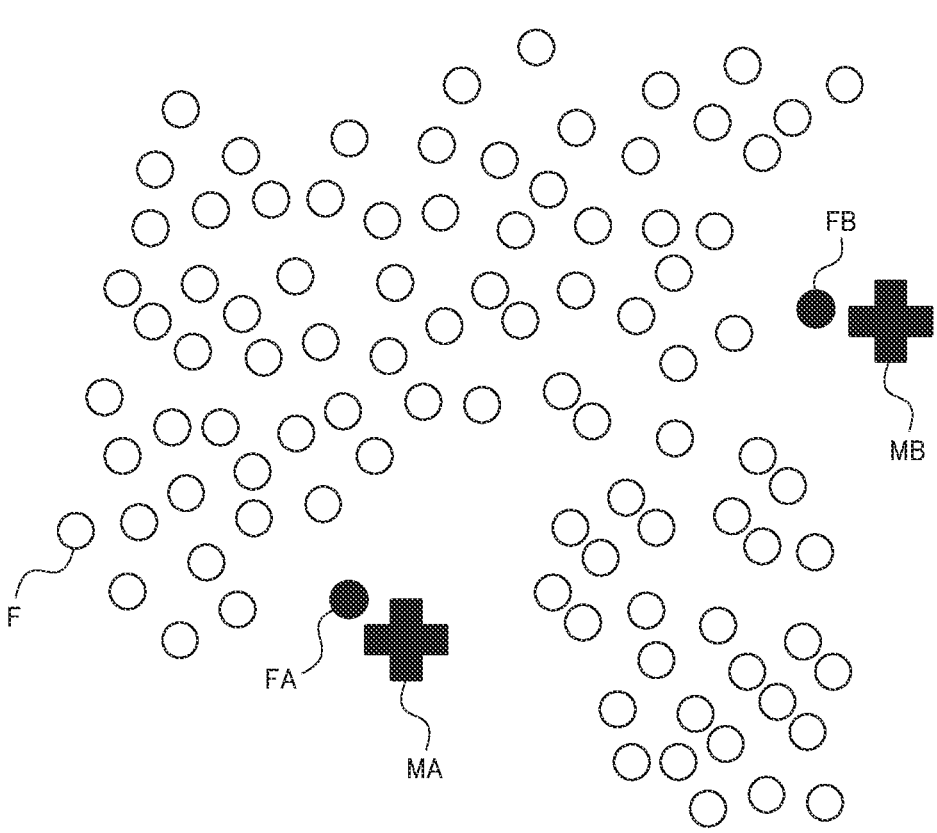
FIG. 18 is an explanatory view of a method for calculating distance between measurement points.

The method of the present embodiment is not limited to those described above, and may be performed in various different ways. As a modification example, for example, when the surgeon sets arbitrary two measurement points MA and MB in the captured image shown in E1 in FIG. 17, the endoscope system 1 may present information between the two measurement points MA and MB to the user in the screen shown in E2. The information between two points refers to the component between the two points in each of the x-direction, y-direction, and z-direction, the length between the two points, the projection length between the two points, and the like. The screen display shown in E2 in FIG. 17 can be performed by the following method. For example, as shown in FIG. 18, it is assumed that the feature points F constituting a three-dimensional structure having a known absolute size value are arranged. The lumen structure calculation section 120 performs a process of extracting a feature point FA that is closest to the measurement point MA and a feature point FB that is closest to the measurement point MB, determining information such as coordinates and distances of the measurement points MA and MB based on coordinate information of the feature point FA and the feature point FB, and transmitting the information to the size estimation section 130. The lumen structure calculation section 120 may determine the coordinates of the measurement points MA and MB and the information between the two points using the coordinate information of a plurality of feature points F that are located in the vicinity of the measurement points MA and MB. The size estimation section 130 then performs a process of outputting screen data based on the information to the monitor 150.

Figure 19:
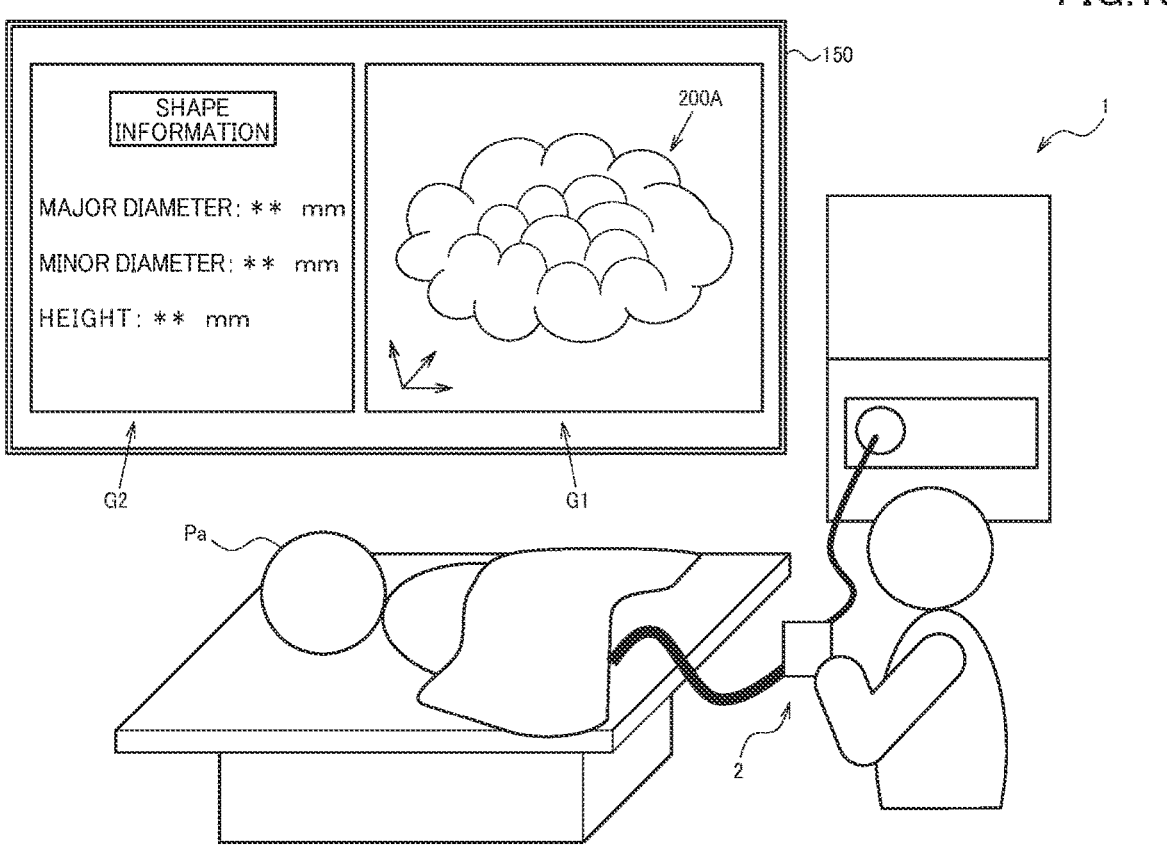
FIG. 19 illustrates another example of display of a monitor in which the method of the present embodiment is applied.

Further, as another modification example, as shown in G1 in FIG. 19, the endoscope system 1 may present a three-dimensional specific portion structure 200A to the user while changing the orientation of the viewpoint. Further, as shown in G2, a major diameter D1, a minor diameter D2, and a height H of the three-dimensional specific portion structure 200A may be presented to the user on the monitor 150. In this way, the user, i.e., the surgeon or the patient Pa, can appropriately understand the specific portion 200.

Figure 20:
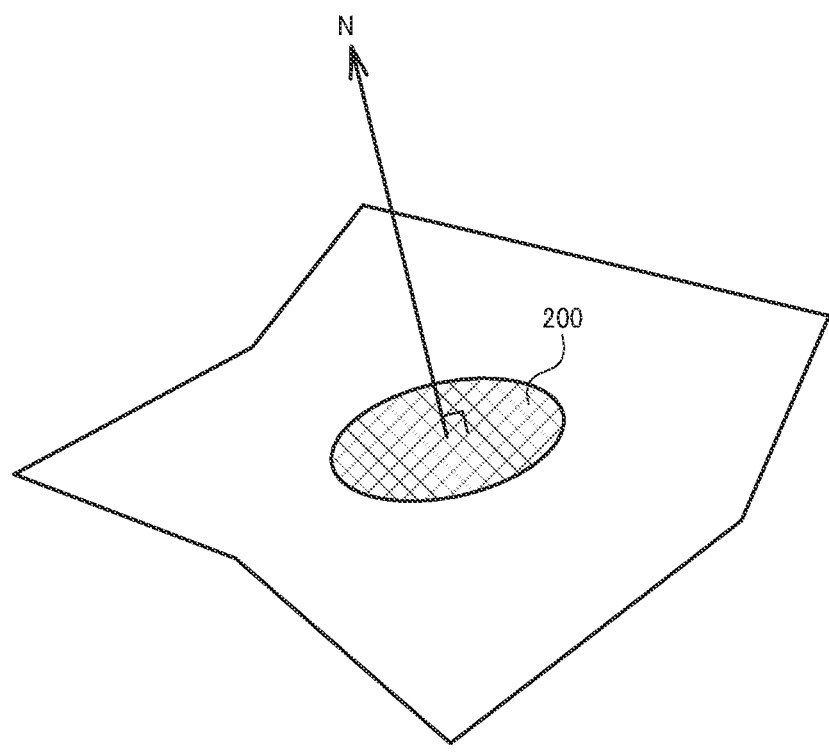
FIG. 20 is an explanatory view of a method for measuring a size of a specific portion.
Figure 21:
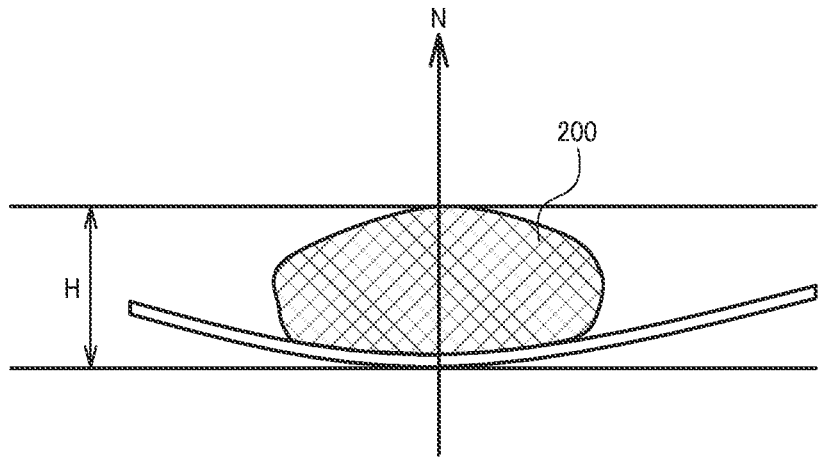
FIG. 21 is another explanatory view of the method for measuring a size of a specific portion.
Figure 22:
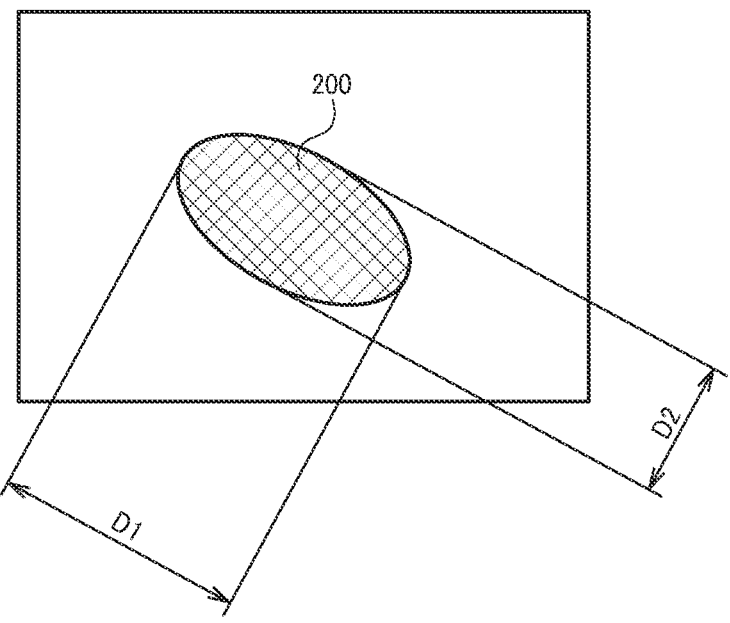
FIG. 22 is another explanatory view of the method for measuring a size of a specific portion.

Since the specific portion structure 200A is a three-dimensional structure and its appearance can change depending on the viewpoint and orientation, the results of size measurement will vary if the size is measured without specifying the line-of-sight direction. Therefore, the three-dimensional structure calculation section of the endoscope system 1 of the present embodiment calculates the major diameter D1, the minor diameter D2, and the height H of the specific portion structure 200A based on an object projected on a plane parallel to the inner wall of the lumen around the specific portion 200, in other words, a plane perpendicular to the normal vector N shown in FIG. 20 and FIG. 21. That is, the height H is a height based on a plane parallel to the inner wall described above, and is the length of the specific portion structure 200A along a direction parallel to the normal vector N, as shown in FIG. 21. Then, as shown in FIG. 22, the major diameter D1 and the minor diameter D2 of the specific portion structure 200A are determined as viewed from a direction perpendicular to the normal vector N. The size estimation section 130 then outputs display data based on these items of information to the monitor 150. As described above, the size estimation section 130 of the endoscope system 1 of the present embodiment outputs the major diameter D1 and the minor diameter D2, i.e., the actual size of the object projected on a plane parallel to the lumen around the specific portion 200 as specific portion size information. In this way, the line-of-sight direction in the measurement of the size of the specific portion 200 is determined, thereby improving the accuracy of the result of the size measurement of the specific portion 200. Further, the size estimation section 130 of the endoscope system 1 of the present embodiment outputs the height H, which is the actual size of the object in the direction perpendicular to the inner wall of the lumen around the specific portion 200, as the specific portion size information. As shown in FIG. 22, in a state where the user observes the specific portion 200 from a direction perpendicular to the normal vector N, the user cannot easily grasp the information of the height H; however, employing the method of the present embodiment enables the user to grasp also the information of the height H of the specific portion 200.

Figure 23:
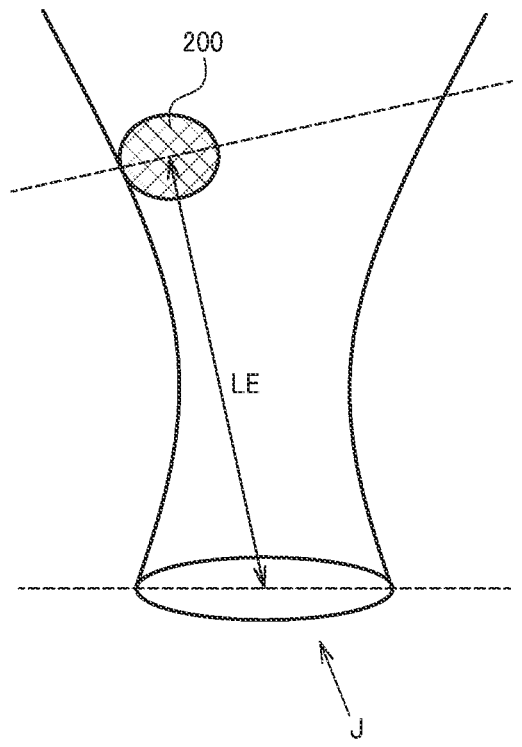
FIG. 23 is an explanatory view of a method for measuring a length from an opening to a specific portion.

Further, although an example of determining the actual size information of the size of the specific portion 200 in the entire three-dimensional structure of the lumen has been described as the method of the present embodiment, the method of the present embodiment is not limited to this example. The endoscope system 1 of the present embodiment may also determine the actual size information of a distance LE from a predetermined opening to the specific portion 200. The distance LE is the distance from the predetermined opening shown in J to the center of the specific portion 200, as shown, for example, in FIG. 23. For example, in the case of observation of large intestine, the predetermined opening is the anus. Further, the center here includes a substantial center. For example, it is assumed that the specific portion 200 is a lesion and that the surgeon is considering the best treatment to remove the specific portion 200 from among a plurality of treatments. Examples of the plurality of treatments include endoscopic removal, surgical removal, and the like. In this case, since the actual size of the distance LE from the predetermined opening to the specific portion 200 can be determined by the method of the present embodiment, the surgeon can select an appropriate treatment from among a plurality of treatments. In addition, since the actual size of the distance LE can be determined, the surgeon can predict the progress after the treatment with a higher degree of accuracy.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

The invention claimed is:

1. An endoscope system comprising:

an insertion section configured to be inserted into a lumen as an object;

a monocular imager provided in the insertion section and configured to capture an image of the object; and a control device including a processor that processes a signal from the imager, wherein the processor is configured to:

acquire actual size determination information for determining an actual size of at least a portion of the lumen;

determine a three-dimensional structure of the lumen based on the captured image;

determine three-dimensional structure size information for determining an actual size of at least a portion of the three-dimensional structure by calibrating the three-dimensional structure of the lumen based on the actual size determination information;

determine a line-of-sight direction with respect to a specific portion, the specific portion being a portion of the lumen for measurement; and output specific portion size information representing an actual size of the specific portion of the three-dimensional structure and a height from an inner wall of the lumen to a maximum extent of the specific portion along a normal line extending from the inner wall of the lumen, based on the three-dimensional structure size information.

2. The endoscope system as defined in claim 1, wherein the processor acquires a size on the captured image of an object for comparison, which appears in the captured image and has a known size, as the actual size determination information.

3. The endoscope system as defined in claim 1, wherein the processor extracts a plurality of feature points from each captured image, calculates a position of each feature point in a three-dimensional space, based on positions of the plurality of feature points on the captured image, and calculates the three-dimensional structure of the lumen, based on the calculated position of each feature point in the three-dimensional space.

4. The endoscope system as defined in claim 3, wherein the processor extracts the specific portion from the captured image and extracts the feature points from the captured image including the specific portion, and associates the extracted feature points with the feature points in the three-dimensional structure to set a position of the specific portion in the three-dimensional structure.

5. The endoscope system as defined in claim 3, wherein the imager acquires the captured image at a plurality of time points, and the processor extracts the feature points that commonly appear in the captured images at the plurality of time points, acquires three-dimensional arrangement information of the insertion section at the plurality of time points based on output of a position sensor that extracts information of at least a portion of position and orientation of the imager, and calculates positions of the feature points in the three-dimensional space based on the three-dimensional arrangement information of the insertion section at the plurality of time points and positions on the captured image of the feature points that commonly appear in the captured images at the plurality of time points.

6. The endoscope system as defined in claim 1, wherein the processor sets the specific portion based on the captured image.

7. The endoscope system as defined in claim 6, wherein the processor presents the specific portion on the captured image in a manner visible to a user.

8. The endoscope system as defined in claim 6, wherein the processor automatically sets the specific portion.

9. The endoscope system as defined in claim 6, wherein the captured image is separable into a plurality of items of color information, and the processor sets the specific portion using first color information included in the plurality of items of color information, and calculates the three-dimensional structure and the three-dimensional structure size information using second color information that is included in the plurality of items of color information and does not include the first color information.

10. The endoscope system as defined in claim 6, wherein a plurality of setting modes are available to select, and the processor sets the specific portion based on the selected setting mode.

11. The endoscope system as defined in claim 6, wherein the processor sets the specific portion based on setting that has been redone in a different setting mode of the same image or using a different image.

12. The endoscope system as defined in claim 1, wherein the processor determines the three-dimensional structure and the three-dimensional structure size information based on the captured image captured within a predetermined time and the actual size determination information acquired within the predetermined time.

13. The endoscope system as defined in claim 1, wherein the processor outputs the actual size of a target object projected on a plane parallel to the lumen around the specific portion as the specific portion size information.

14. The endoscope system as defined in claim 1, wherein the processor outputs the actual size of a target object in a direction perpendicular to the lumen around the specific portion as the specific portion size information.

15. The endoscope system as defined in claim 1, wherein the processor determines three-dimensional structure information with the actual size based on the actual size determination information.

16. The endoscope system as defined in claim 1, wherein the processor outputs the specific portion size information in association with information of the three-dimensional structure of the specific portion.

17. The endoscope system as defined in claim 1, wherein the major diameter, the minor diameter, and the height of the specific portion are output based on an object projected on a plane perpendicular to the normal line from a plane parallel to the inner wall of the lumen around the specific portion.

18. The endoscope system as defined in claim 17, wherein the height is based on a plane parallel to the inner wall, and is the length of the specific portion along a direction parallel to the normal vector.

19. The endoscope system as defined in claim 1, wherein, as the actual size, a distance from a predetermined location, representing an anatomical entry point of the lumen, to the specific portion is calculated and output.

20. The endoscope system as defined in claim 1, wherein the specific portion is displayed on a monitor to the user while changing the line-of-sight direction.

21. The endoscope system as defined in claim 1, wherein the actual size of the three-dimensional structure is calculated.

22. The endoscope system as defined in claim 1, wherein the actual size of the three-dimensional structure and the actual size of the specific portion are displayed on a monitor at the same time.

23. A lumen structure calculation system comprising a processor including hardware, wherein the processor;

acquires a captured image of an object acquired by a monocular imager provided in an insertion section, which is inserted into a lumen as the object, and actual size determination information, which is information for determining an actual size of at least a portion of the lumen;

determines a three-dimensional structure of the lumen based on the captured image;

determines three-dimensional structure size information for determining an actual size of at least a portion of the three-dimensional structure by calibrating the three-dimensional structure of the lumen based on the actual size determination information;

determine a line-of-sight direction with respect to a specific portion, the specific portion being a portion of the lumen for measurement; and outputs specific portion size information representing an actual size of the specific portion of the three-dimensional structure and a height from the inner wall of the lumen to a maximum extent of the specific portion along a normal line extending from the inner wall of the lumen, based on the three-dimensional structure size information.

24. A method for creating lumen structure information comprising:

acquiring a captured image of an object acquired by a monocular imager provided in an insertion section, which is inserted into a lumen as the object;

acquiring actual size determination information, which is information for determining an actual size of at least a portion of the lumen;

determining a three-dimensional structure of the lumen based on the captured image;

determining three-dimensional structure size information for determining an actual size of at least a portion of the three-dimensional structure by calibrating the three-dimensional structure of the lumen based on the actual size determination information;

determining a line-of-sight direction with respect to a specific portion, the specific portion being a portion of the lumen for measurement; and outputting specific portion size information representing an actual size of the specific portion of the three-dimensional structure and a height from the inner wall of the lumen to a maximum extent of the specific portion along a normal line extending from the inner wall of the lumen, based on the three-dimensional structure size information.

* * * * *